US012793830B1

(12) United States Patent
Howe

(10) Patent No.: US 12,793,830 B1
(45) Date of Patent: Nov. 10, 2026

(54) SYSTEMS AND METHODS FOR PROVIDING THERAPEUTIC ENDO-KINETIC DEVICE TREATMENTS IN COMBINATION WITH MONTHLY POINTS DRIVEN MEMBERSHIPS IN A RETAIL FACILITY

(71) Applicant: DryRx, LLC, Fort Collins, CO (US)

(72) Inventor: Todd Howe, Fort Collins, CO (US)

( * ) Notice: Subject to any disclaimer, the term of this patent is extended or adjusted under 35 U.S.C. 154(b) by 606 days.

(21) Appl. No.: 17/649,438

(22) Filed: Jan. 31, 2022

Related U.S. Application Data

(60) Provisional application No. 63/143,142, filed on Jan. 29, 2021.

(51) Int. Cl.

| | |
|---|---|
| ***A61H 9/00*** | (2006.01) |
| ***G06Q 10/10*** | (2023.01) |
| ***G06Q 10/1093*** | (2023.01) |
| ***G06Q 30/0601*** | (2023.01) |
| ***G16H 20/30*** | (2018.01) |

(52) U.S. Cl.
CPC ........... *G16H 20/30* (2018.01); *A61H 9/0021* (2013.01); *G06Q 10/1093* (2013.01); *G06Q 30/0641* (2013.01); *A61H 2201/5035* (2013.01); *A61H 2201/5043* (2013.01)

(58) Field of Classification Search
CPC ...... G16H 20/30; G16H 40/63; A61H 9/0021; A61H 2201/502; A61H 9/00; A61H 2009/0035; A61H 2009/0042; A61H 2201/5035; A61H 2201/5038; A61H 2201/5043; A61H 2201/5046
See application file for complete search history.

(56) References Cited

U.S. PATENT DOCUMENTS 4,635,620 A * 1/1987 Ricchio .................. A61H 23/04 5/672
7,249,039 B2 * 7/2007 Yoshioka ............... G06Q 30/02 705/4
8,458,051 B1 * 6/2013 Saltzman ............... G06Q 50/10 705/26.7
2003/0033666 A1 * 2/2003 Hutsell .................... A61H 9/00 4/584
2004/0059633 A1 * 3/2004 Rankin .................. G06Q 50/12 705/15
2006/0265341 A1 * 11/2006 Strickon ............ G06Q 10/0875 705/402

(Continued)

OTHER PUBLICATIONS

English translation of Cho et al. (WO 2020/032328 A1) (Year: 2020).*
English translation of Sartor (EP 1757260 A1) (Year: 2007).*

*Primary Examiner* — Timothy A Stanis
*Assistant Examiner* — Christopher E Miller

(57) ABSTRACT

Systems and methods for providing a special assortment of Endo-Kinetic therapeutic treatments in a retail facility. A commercial retail facility is equipped with dry hydrotherapy massage systems, as well as a plurality of other Endo-Kinetic treatments including sauna treatment systems, Cryotherapy, sequential compression, Contrast Therapy, and Full spectrum therapeutic lighting. The system incorporates membership structures with assignable points in which members utilize their points based on their monthly membership for access to each piece of equipment as well as the health and wellness services and products provided.

9 Claims, 17 Drawing Sheets

(56) References Cited

U.S. PATENT DOCUMENTS

| | | | | | |
|---|---|---|---|---|---|
| 2007/0033069 | A1* | 2/2007 | Rao | A63B 71/0622 | 482/8 |
| 2007/0100261 | A1* | 5/2007 | Turell | A61H 9/0071 | 601/55 |
| 2007/0112600 | A1* | 5/2007 | Palmer | G06Q 99/00 | 705/5 |
| 2008/0039750 | A1* | 2/2008 | Mahmoud | A61H 9/0021 | 601/55 |
| 2008/0312563 | A1* | 12/2008 | Galyean | A61H 33/005 | 607/104 |
| 2011/0055720 | A1* | 3/2011 | Potter | G06F 3/0481 | 709/217 |
| 2011/0258069 | A1* | 10/2011 | Basham | G06Q 30/08 | 705/26.3 |
| 2012/0096637 | A1* | 4/2012 | Laflamme | G06F 1/1626 | 715/771 |
| 2013/0053218 | A1* | 2/2013 | Barker | G16H 20/30 | 482/4 |
| 2013/0325491 | A1* | 12/2013 | Ferrari | G16H 40/63 | 705/2 |
| 2014/0067097 | A1* | 3/2014 | Harris | A63B 71/06 | 700/91 |
| 2014/0156373 | A1* | 6/2014 | Roberts | H04N 21/4882 | 705/14.35 |
| 2015/0335523 | A1* | 11/2015 | Kang | G16H 20/30 | 4/541.1 |
| 2016/0008568 | A1* | 1/2016 | Attia | A61B 5/486 | 600/28 |
| 2016/0206506 | A1* | 7/2016 | Henkemans | A61H 9/0021 | |
| 2019/0298256 | A1* | 10/2019 | Hunt | A61B 5/746 | |
| 2020/0357046 | A1* | 11/2020 | McGann | A61H 23/006 | |
| 2020/0390644 | A1* | 12/2020 | Yang | A61H 15/00 | |
| 2021/0236365 | A1* | 8/2021 | Zilberman | A61N 5/0618 | |
| 2022/0004998 | A1* | 1/2022 | Zhang | G06Q 10/1095 | |

* cited by examiner

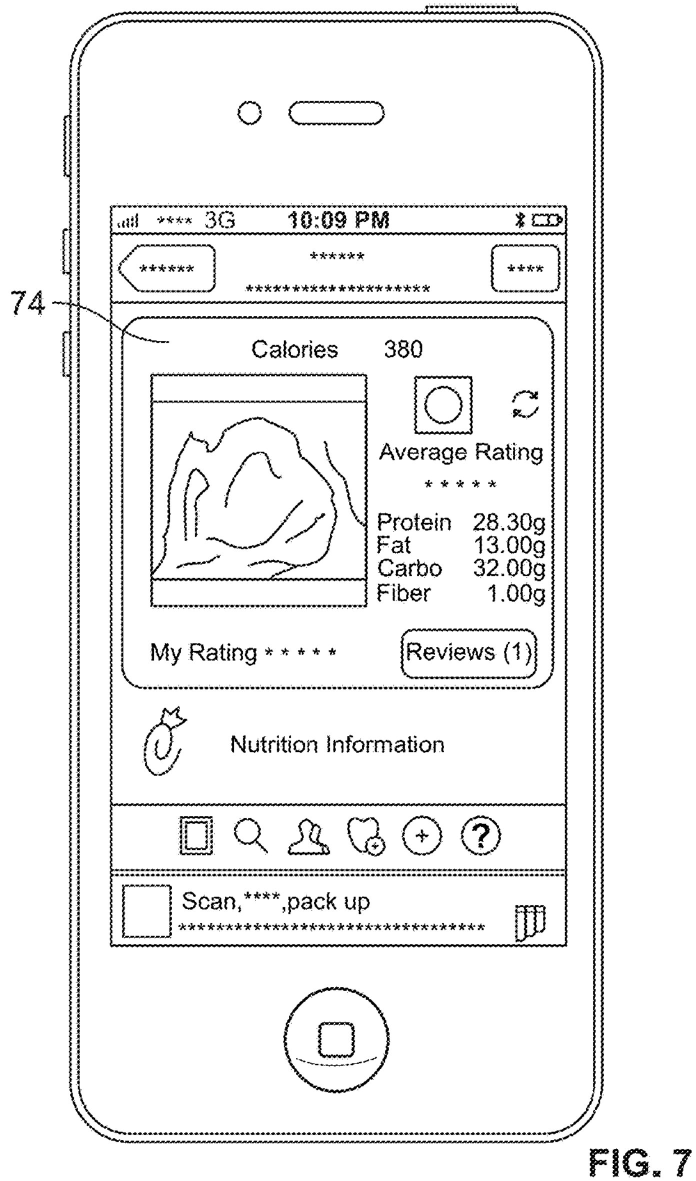
FIG. 7
BODYSTOP
| | Premium Membership | Express Membership | Massage Membership |
|---|---|---|---|
| Massage Sessions | Unlimited | 10 Sessions | 5 Sessions |
| Monthly Pricing | ***$149*** | ***$89*** | ***$49*** |
FIG. 8
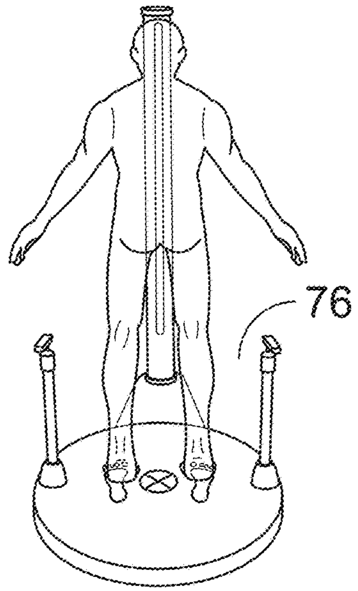
FIG. 9

Monthly Care Packages

| | | Points |
|---|---|---|
| Express | $49 | 5 |
| Wellness | $99 | 15 |
| Signature | $149 | 30 |
| Ultimate | $249 | 60 |

FIG. 20A

Care Packs

| | | Points |
|---|---|---|
| Single Point | $19 | 1 |
| 10 Pack | $99 | 10 |
| 30 Pack | $249 | 30 |

FIG. 20B

SYSTEMS AND METHODS FOR PROVIDING THERAPEUTIC ENDO-KINETIC DEVICE TREATMENTS IN COMBINATION WITH MONTHLY POINTS DRIVEN MEMBERSHIPS IN A RETAIL FACILITY

CROSS-REFERENCE TO RELATED APPLICATIONS

This application claims the benefit of the filing date of U.S. Provisional Application Ser. No. 63/143,142, filed on Jan. 29, 2021, entitled "Systems and Methods for Providing Dry Hydrotherapy Massage and Monthly Massage Memberships in a Retail Facility", as well as the entire disclosure of which is hereby incorporated by reference into the present disclosure. This application hereby incorporates by reference U.S. application Ser. No. 16/905,564, filed Aug. 25, 2020, entitled "Water Encapsulated and Mechanical Hybrid Body Massage Chair with Rapid Heating and Cooling Control", in its entirety. Further, the application hereby incorporates by reference U.S. Provisional Application Ser. No. 63/278,256, Filed Nov. 11, 2021, entitled "Rapid Heating and Cooling Reclining System Utilizing Mechanical and Water Encapsulated Thermal and Massaging Therapy", in its entirety.

FIELD OF THE INVENTION

The present invention relates to Endo-Kinetic related wellness therapies, and specifically to facilities and methods for providing wellness therapies focusing on touch-less treatments to include dry hydrotherapy massage, as well as potential ancillary services which may include sauna, cryotherapy, contrast therapy, body analysis, cardio training, effusion therapy, nutrition, and hydration.

BACKGROUND

The global health and wellness industry is growing rapidly with revenues, according to some estimates, exceeding $2-3 trillion per year. According to surveys conducted by the Centers for Disease Control and Prevention, more than two-thirds of adults in the United States are considered overweight or obese, with more than one-third of adults being considered obese. Yet, despite these market forces, some estimates indicate that less than 20% of the population of the United States is a member of a health club or fitness center. These two overwhelming national statistics, the growth of wellness dollars spent and the continuing growth rate of the overweight/obese populations, underscore the interest and need of people to look and feel better. Unfortunately, convenient and regular access to massage is simply unaffordable to the majority of the population. Additionally, now more than ever, people suffer tension and stress, chronic pain, lack of exercise, and a broad range of conditions which are often best treated with Endo-Kinetic forces. The CDC now estimates that 80% of The US public does not exercise as much as they need to which creates a real shortage of exercise and leads to a number of complications. Using simple kinetic forces on the body mimics much of the benefit found in exercise. So what a vitamin is to a poor diet, so is the kinetic therapy devices to proper exercise.

Segments of the population which either need or often seek information and opportunity for improving personal health and wellness include those people who are overweight or obese, senior citizens, people who are already active and fit, and those people who suffer with chronic pain.

Most people fall into one or more of these categories. These key demographics include: an overweight population exceeding 130 million; those purchasing hands-on massage numbering 40 million; active fitness individuals exceeding 35 million in number; chronic pain sufferers being approximately 95 million people; and a senior citizen population of over 40 million, which is the fastest growing population segment.

Often, those who are overweight or obese may feel out of place in a health club and may be too embarrassed or uncomfortable receiving a hands-on massage or receiving treatments involving human interaction. Yet, these same people want and need the benefit and results that exercise and Endo-Kinetics can deliver. The overweight population is thought to be highly interested in receiving touchless treatments due to the discreet nature of privacy as compared to traditional services.

Senior citizens represent a large and growing segment of the population. More and more seniors are actively seeking information about how to improve mobility and achieve better health. Delivery of concise and accurate information, as well as the provision of helpful and needed services, can help seniors better understand how their health and bodies change over time.

Active people are more likely to know and understand the benefit of Endo-Kinetics, exercise and nutrition and the role that each plays in maintaining a healthful and more enjoyable lifestyle. Such people who already care enough to exercise are more likely to be inclined to want to enhance their fitness quest with the systems and methods disclosed herein.

Health and wellness services, most particularly the type of Endo-Kinetics treatments which is a component of the system and methods herein described, is especially meaningful with respect to a number of chronic pain conditions due to the analgesic benefits of penetrating cold and heat, deep tissue massage, sequential compression, and vibration. In many instances, people who suffer from chronic pain are prescribed massage as a therapy or treatment as a method for relieving the pain. Leading healthcare professionals generally agree that massage not only feels good but is very beneficial to a person's overall health.

The current massage retail environment is cost prohibitive for many individuals, and many customers complain about the difficulty in scheduling sessions as well as the poor quality or inconsistency of the massage service and now an aversion to touch which has increased due to the COVID-19 pandemic.

Dry hydrotherapy massage, by itself or in combination with other Endo-Kinetic therapies and products described herein, are critical factors for the majority of people for achieving and maintaining better health. Moreover, the effects of a one-hour hands-on massage can be felt in as little as a 15-minute dry hydrotherapy massage session. There is a need for having access to such therapies in a one-stop facility and providing these therapies at a more affordable price point which markedly increases accessibility to such beneficial therapies, all delivered in a comfortable spa-like environment.

Some unique preferred embodiments of the present invention include: 10 no other free standing dedicated dry-hydrotherapy/Endo-Kinetic facilities, 2) no other massage related business is offering a similar month pricing membership strategy, 3) no other facility uses smartphone or kiosk scheduling technology, and 4) no other facility has a user customized massage pre-programming feature.

BRIEF SUMMARY OF THE INVENTION

A principal object of the present invention is to provide the novel dry hydrotherapy system by itself and in combination with other beneficial Endo-Kinetics therapies in a single location in a manner which enhances accessibility to such cost effective therapies. Another object is to combine benefits and therapies in a single system to save time, cost and frustration for operators and users.

The systems and methods of this disclosure are directed to what is being referred to as "endo-kinetics" or the internal effect of kinetic force is applied to the body to achieve a benefit similar to exercise in a passive sense. Currently there is no other provider or business that is offering a specially selected full spectrum of Endo kinetic devices combined with a novel delivery method which includes a cloud based membership with a point system that allows the member to choose treatments based on the body's needs/preference within a controlled spa-like environment. This control system can be driven through a personal application of a mobile device to manage membership and even schedule sessions on a specific device. As will be described in greater detail below, endo kinetics encompasses high performance devices that provide a massaging action, sequential compression force, extreme temperature variation (cryo-therapy) and vibration which are the main mechanisms of therapy.

To those ends, among others, the present invention includes systems and methods for providing a safe and aesthetically appealing user support that optimizes conditions for the user while providing dry hydrotherapy and Endo-Kinetics treatments, augmented by thermal, visual, olfactory, and auditory sources, in a commercial environment. Embodiments of the invention provide safe, comfortable, and healthy support with optimal therapy.

Other objects of the invention include the provision of complementary wellness benefits including a sauna system. In some preferred embodiments, such a system more particularly would be an infrared sauna system. Other components of the preferred system embodiments include access other Endo-Kinetic therapies, and healthful, related products.

Another object of the present invention includes the system having a membership structure wherein persons can pay a reoccurring monthly fee for a membership for having convenient and affordable access to the system facility as well as access to the wellness therapies and other amenities herein described. Some embodiments include a tiered membership program providing different amounts of access time to the facility amenities based on different price and point structures. Alternative embodiments may also include access to devices and technology for performing body analysis.

It is also contemplated that spaces within the facility will incorporate tables and chairs for members to relax. The facility may provide complimentary Wi-Fi service for the use and enjoyment of members who use the various other services provided at the facility to help stimulate the mind and body effects from relaxation.

The disclosure, including descriptions, drawings, and claims, describes one or more embodiments of the invention. Many other features, objects, and advantages of the invention will be apparent to one of ordinary skill in the art from the disclosure. Given the disclosure, especially in light of the prior art, it is another object of the invention to improve upon, and overcome the inefficiencies, limitations, and constraints of, the prior art.

BRIEF DESCRIPTION OF THE DRAWINGS

FIG. 7 illustrates a software application as it appears on a smartphone display.

FIG. 8 is a chart showing one non-limiting example of a membership pricing structure.

FIG. 9 illustrates a body analyzer as a possible component of alternative embodiments of system.

FIG. 20A is a table illustrating monthly care packages according to the system disclosed.

FIG. 20B is a table illustrating care packs according to the system disclosed.

DETAILED DESCRIPTION OF PREFERRED EMBODIMENTS

The following descriptions relate to presently preferred embodiments and are not to be construed as describing limits to the invention, whereas the broader scope of the invention should instead be considered with reference to the claims, which may be now appended or may later be added or amended in this or related applications. Unless indicated otherwise, it is to be understood that terms used in these descriptions generally have the same meanings as those that would be understood by persons of ordinary skill in the art. It should also be understood that terms used are generally intended to have the ordinary meanings that would be understood within the context of the related art, and they generally should not be restricted to formal or ideal definitions, conceptually encompassing equivalents, unless and only to the extent that a particular context clearly requires otherwise.

For purposes of these descriptions, a few wording simplifications should also be understood as universal, except to the extent otherwise clarified in a particular context either in the specification or in particular claims. The use of the term "or" should be understood as referring to alternatives, although it is generally used to mean "and/or" unless explicitly indicated to refer to alternatives only, or unless the alternatives are inherently mutually exclusive. When referencing values, the term "about" may be used to indicate an approximate value, generally one that could be read as being that value plus or minus half of the value. "A" or "an" and the like may mean one or more, unless clearly indicated otherwise. Such "one or more" meanings are most especially intended when references are made in conjunction with open-ended words such as "having," "comprising" or "including." Likewise, "another" object may mean at least a second object or more.

Figure 1:
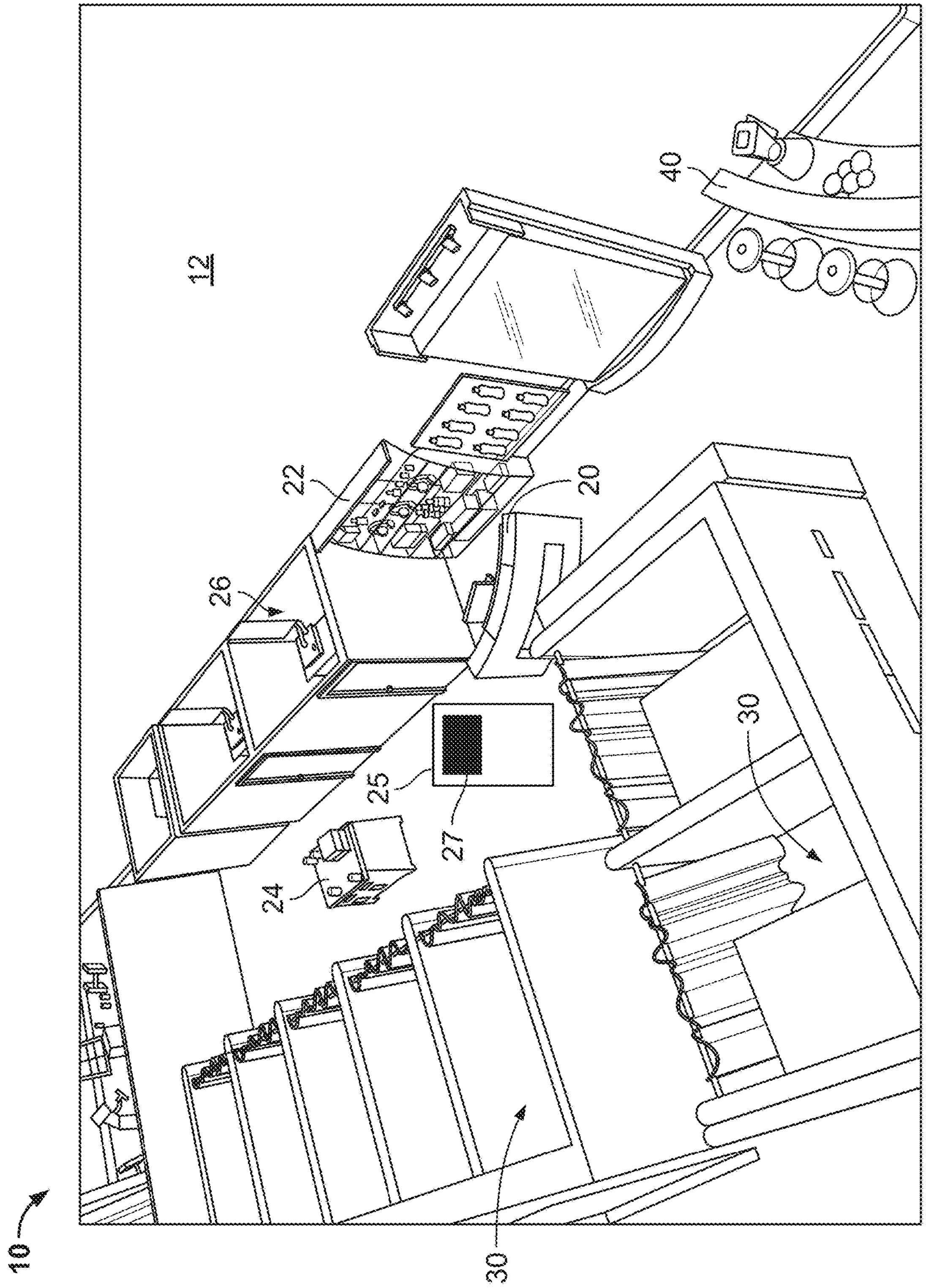
FIG. 1 illustrates an embodiment showing placement of system elements within a facility.

As shown in FIG. 1, some preferred embodiments of the present invention involve a system 10 implementing the provision of dry hydrotherapy massage along with various other complementary health and wellness therapies and products and incorporating a retail facility 12 (also referred to as a "Relaxation Center") operated in a manner related to the provision of various health and wellness therapies. Facility 12 is preferably a building, either stand-alone or as part of a complex in the nature of a shopping center housing other retail establishments. Preferred embodiments of system 10 include facility 12 having adequate space for arranging a number of other system components, as described below, which can accommodate a large number of users of such system components at any one time.

Preferred embodiments of system 10 provide the health and wellness services and products within a membership program. Individual memberships can be established wherein a member remits periodic payments for access to facility 12 and the various services and products offered, as described in further detail below. Some embodiments of system 10 also contemplate that at the same time the various services and products available at facility 12 are offered within the context of a membership structure, these services and products may also be obtained as separately priced items outside of the membership program by those who choose not to secure a membership. Further details of membership structure and pricing are discussed below with regard to the chart illustrated in FIG. 8.

Facility 12 is shown with various services and products available. Service center 20 provides a purchase point for various health and fitness related products shown in product display 22. Shown adjacent to service center 20 is beverage station 40, wherein it is contemplated a variety of healthful fresh juices, smoothies, and other assorted health-related beverages are offered. Facility 12 also includes a check-in kiosk 25 which includes a graphical user interface 27 that users can interact with to customize various therapy sessions offered by facility 12 using their subscription-based plan with the facility 12, as discussed in greater detail below.

Private therapy rooms 30 are also shown in FIG. 1, wherein members or non-members can receive a variety of health and wellness therapies. Therapy rooms 30 are configured to accommodate a dry hydrotherapy massage system 50, an example of such dry hydrotherapy massage system being shown in FIG. 2A.

A major focus of system 10 is making an effective form of massage therapy, and more specifically, endo-kinetic treatment, that is affordable and accessible while combining complimentary wellness tools and benefits. One of the endo-kinetic treatments of system 10 is provided by dry hydrotherapy massage system 50. In contrast to hands-on massage techniques, the dry hydrotherapy massage system 50 incorporates powerful hydrotherapy jets to create a consistent touchless massage. With respect to the effectiveness of dry hydrotherapy massage system 50, a 15-minute massage session feels similar and has similar benefits to an hour long traditional hands-on massage.

Figure 2A:
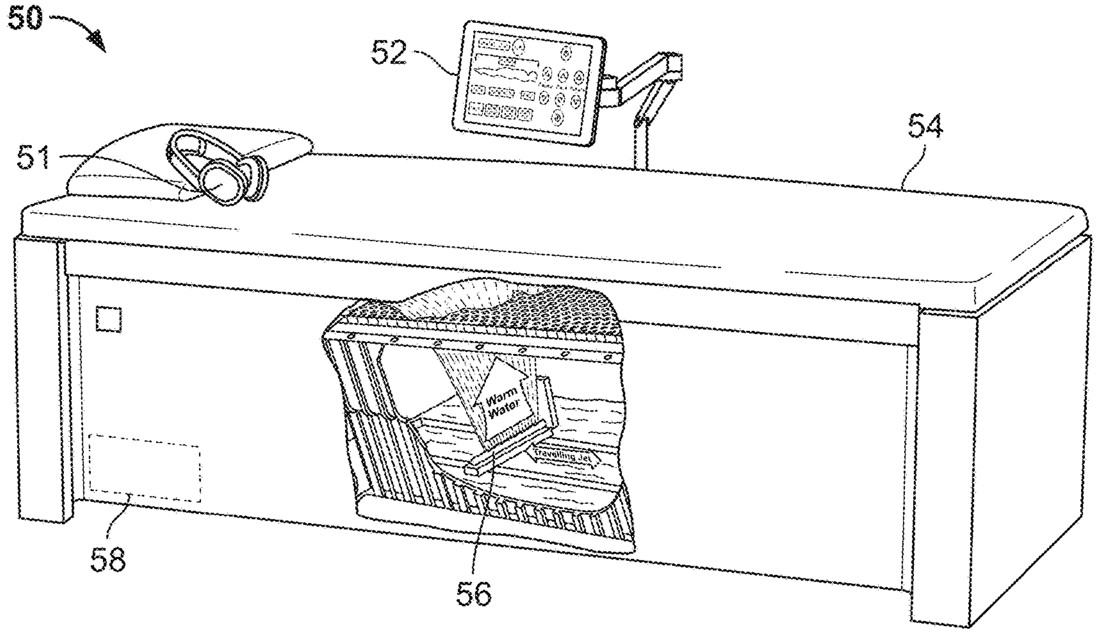
FIGS. 2A-2H show a preferred dry hydrotherapy massage system as a component of a system for use in a facility, as well as screenshots of various menu screens provided by a touchscreen of the facility.

Also incorporated in the dry hydrotherapy massage system 50 is advanced sound suppression as well as the opportunity to have relaxation music delivered through noise-cancelling headphones 51. Benefits to a user of dry hydrotherapy massage system 50 include, but are not limited to, pain reduction, lymphatic stimulation, improved circulation, relaxation, and reduced stress. The dry hydrotherapy massage system 50 integrates custom massage programs, and its touchless operation appeals to those segments of the population who are averse to touch, and who therefore would likely avoid a traditional hands-on massage. Preferred dry hydrotherapy massage systems 50 include the Solajet™ Drywave™ Massage System manufactured by Drywave Technologies Inc, as shown in FIG. 2A. This particular dry hydrotherapy massage system 50 is a registered FDA Class 1 medical device.

As shown in FIG. 2A, dry hydrotherapy massage system 50 includes an input device connected or in proximity to dry hydrotherapy massage system 50 for interacting with and operating the system 50, such as graphical user interface 52 as shown in FIG. 2A. Graphical user interface 52 is also referred to as a touchscreen throughout this application. Touchscreen 52 may be connected to dry hydrotherapy massage system 50 in a wired or wireless configuration. Touchscreen 52 is mounted so as to allow a user of dry hydrotherapy massage system 50 to interact with touchscreen 52 while on or using dry hydrotherapy massage system 50. Mounting of touchscreen 52 may be accomplished by any suitable method such as by an adjustable stand as shown in FIG. 2A. System 50 has a user platform 54 upon which the user lays or sits to receive the massage therapy performed by system 50. System 50 also a water jets system 56 configured to eject water at the platform 54 to provide the massage therapy to the user. Accordingly, system 50 can be referred to as a dry hydrotherapy massage system, as it provides massage therapy using pressurized water ejected against the user platform 54. The water jet system 56 can comprises a plurality of water jets configured to eject water at the platform 54. Water jet system 56 can eject water a variable water pressures according to preferences set by the user, as will be discussed in detail below. Additionally, water jet system 56 can comprise water heaters and water coolers so that heated and cooled dry hydrotherapy can be provided by the system 50. System 50 further comprises a control system 58 configured to communicate with graphical user interface 52 and control operation of water jet system 56 based on the communication with graphical user interface 52. As will be discussed in detail below, control system 58 controls water jet system 56 based on inputs made by the user at graphical user interface 52. Additionally, as will be discussed in greater detail below, control system 58 is configured to communicate with graphical user interface 27 of kiosk 25 and control water jet system 56 based on inputs made by the user at graphical user interface 27. One with skill in the art will recognizes that control system 58 include various hardware components for performing the operations described, such as, for example, memory storages, processors, controllers, and/or servers. Those with skill in the art will understand that in various embodiments, other endo-kinetic systems and devices are equipped with controllers and user interfaces substantially the same as those of massage system 50. Control system 58 and touchscreen 52 are shown as being used with system 50 as a mere illustration of one of the many embodiments of the disclosure.

It is also contemplated that system 10 will include kiosks 25 at convenient locations within facility 12 which incorporate touchscreens 27 for a customer to use in accordance with the description in the following paragraphs. More particularly, it is contemplated that customers can register for or order services using touchscreen 27 integrated with such in-store kiosks 25. Accordingly, touchscreen 27 is configured to communicate with each of the control systems 58 of the facility 12 to control a massage experience, as will be discussed in greater detail below. Registration may also occur through the same or similar methods using a smartphone software application or through a secure web-based portal, all in the nature of a "massage on demand" experience.

Referring now to FIGS. 2B-2H, there are shown screenshots of a preferred embodiment exhibiting various options for a user to build a "USER CUSTOMIZED PRESET MASSAGE" wherein the user is able to customize the dry hydrotherapy massage experience and to interact with and operate dry hydrotherapy massage system 50 to select various options for a dry hydrotherapy massage through the course of accessible menus presented on touchscreens 52, 27 as described in further detail below. At the outset, as will be understood by those of ordinary skill in the relevant art, the menu displays as shown on touchscreens 52, 27 are merely for illustrative purposes only and are only examples of a preferred embodiment of the system 10. Other facets of operating dry hydrotherapy massage system 50 may be represented in other embodiments, and those operational characteristics which are represented in FIGS. 2B-2H may appear differently in alternative embodiments than their appearance as presently shown. Any such alternate displays are intended to be within the scope of the present disclosure.

Figure 2B:
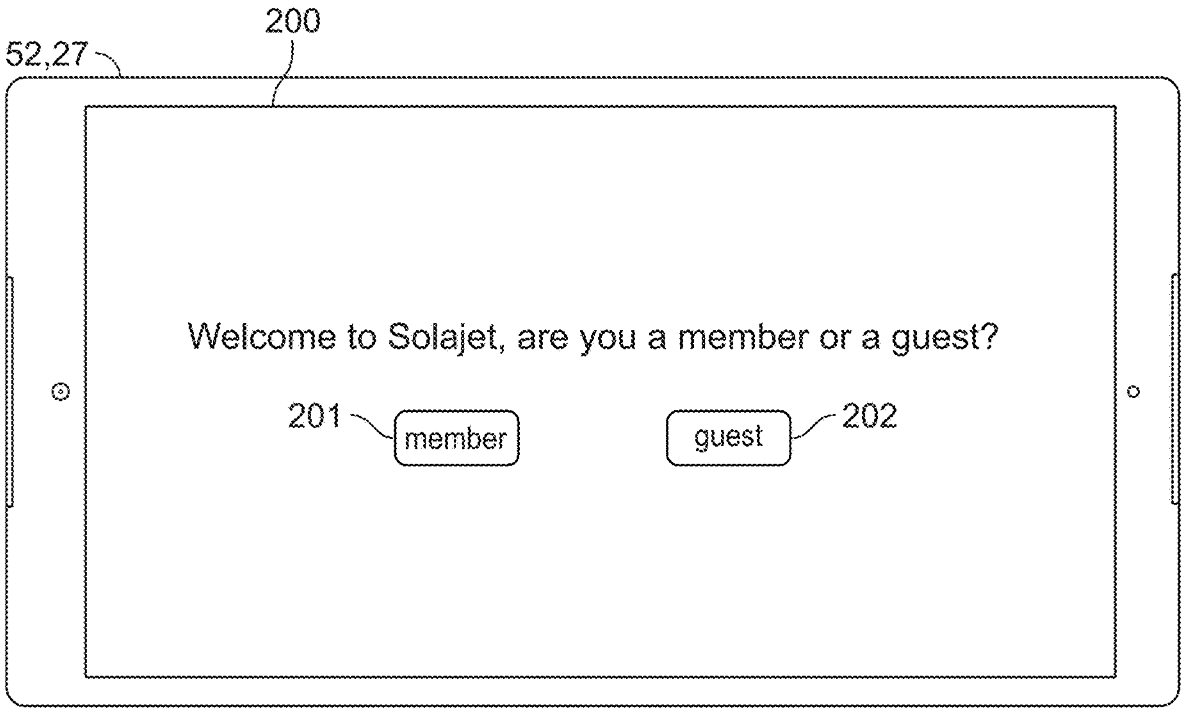

FIG. 2B displays an introductory menu 200 screen or "Welcome" menu screen which requests that a user select either "Member" 201 or "Guest" 202 options in order to proceed through to the other steps in customizing the dry hydrotherapy massage experience. As illustrated in FIG. 2B, in some embodiments introductory screen 200 is presented on touchscreen 52, and in some embodiments introductory screen 200 is presented on touchscreen 27.

Figure 2C:
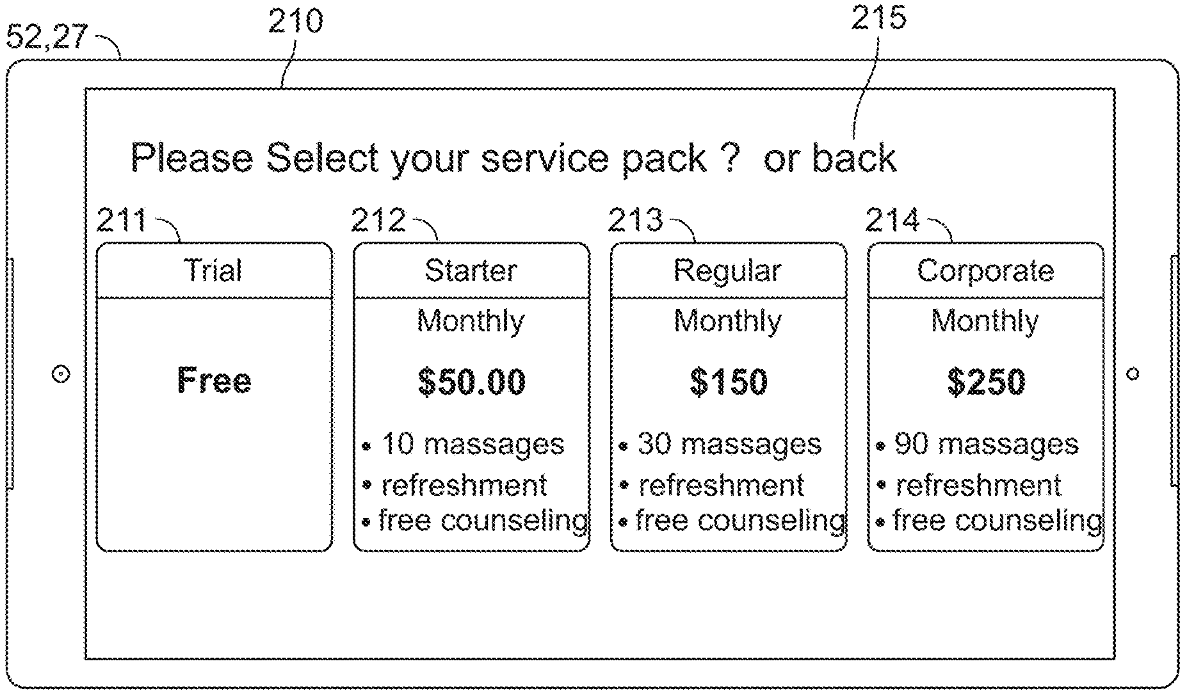

FIG. 2C illustrates a membership subscription plan menu page 210 on the touchscreen 52, 27 with a plurality of icons 211-215 that are selectable by the user. As illustrated in FIG. 2C, in some embodiments subscription plan page 210 is presented on touchscreen 52, and in some embodiments subscription plan page 210 is presented on touchscreen 27. Subscription plan page 210 allows the user to choose a subscription plan membership tier option 212-214 or, as an example, to select the option of proceeding with a "Free Trial" option 211 use of dry hydrotherapy massage system 50. Subscription plan option icons include "Starter" 212, "Regular" 213, and "Corporate" 214 membership options. The "Starter" membership option 212 provides 10 massages with massage system 50, refreshments, and free counseling for a subscription cost of $50 a month. The "Regular" membership option 213 provides 30 massages with massage system 50, refreshments, and free counseling for a subscription cost of $150 a month. The "Corporate" membership option 214 provides 90 massages with massage system 50, refreshments, and free counseling for a subscription cost of $250 a month. In some embodiments, instead of listing a number of massages included in each package, each icon 211-214 displays a certain number of points that are associated with each subscription option. As discussed in greater detail below with reference to FIGS. 20A and 20B, the points can be redeemed for therapeutic session with any of the endo-kinetic systems devices within facility 12. The user also has the option of returning to an earlier menu screen by selecting the "back" option 215 as shown at the top of the display of touchscreen 52.

Figure 2D:
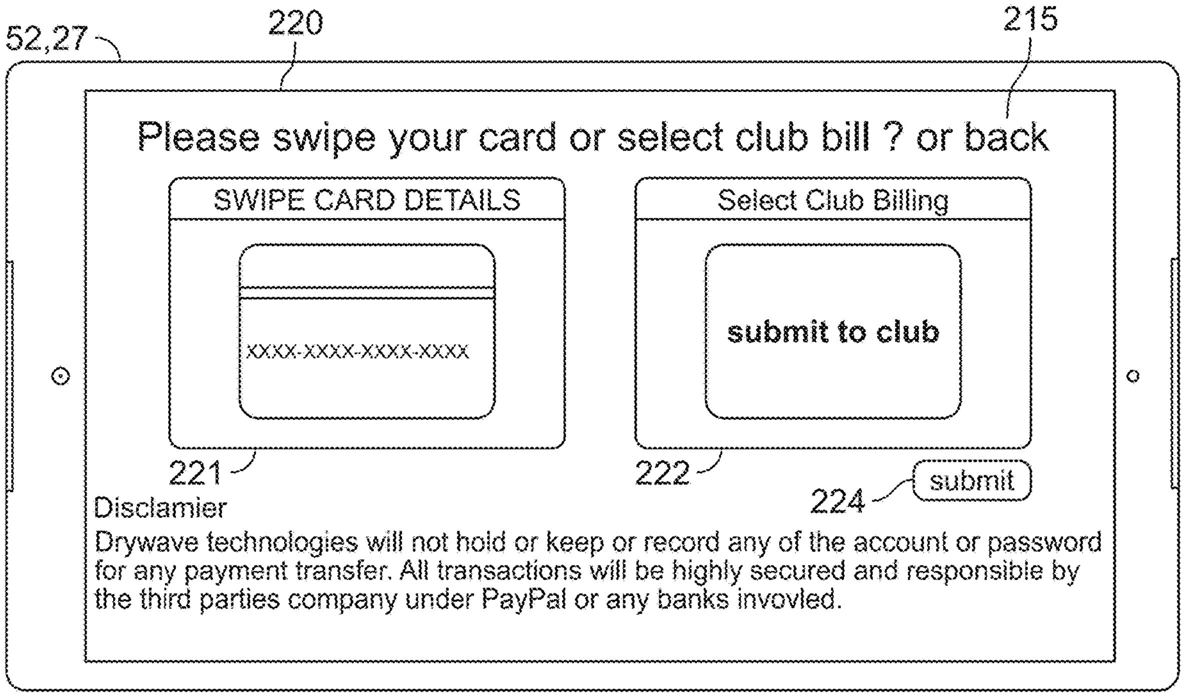

As illustrated in FIG. 2D, after selecting a membership tier 212-214 or Free Trial 211, from the membership selection menu 210 the user is then presented with a subscription plan payment page 220 on the touchscreen 52, 27 for electing a payment method for the membership tier 211-214 selected by the user. Those skilled in the art will recognize that the examples provided can include various other alternative options for names, number of treatments, and services provided. A user may choose to pay using a credit or debit card option by selecting icon 221 or a user may elect the "Club Billing" option by selecting icon 222 in which the user would be billed at a later date rather than paying for the service at the time the service is received. If payment icon 221 is selected, the user can swipe their debit/credit card in a card reader of the massage system 50 or the kiosk 25, or may enter the card information manually on the graphical user interface 52, 27. Once the selection of a payment method has been made, the user then presses the "Submit" icon 224 on touchscreen 52, 27 to continue through to the next display menu page. The user also has the option of returning to an earlier menu screen by selecting the "back" option icon 215 as shown at the top of the display of touchscreen 52, 27.

Figure 2E:
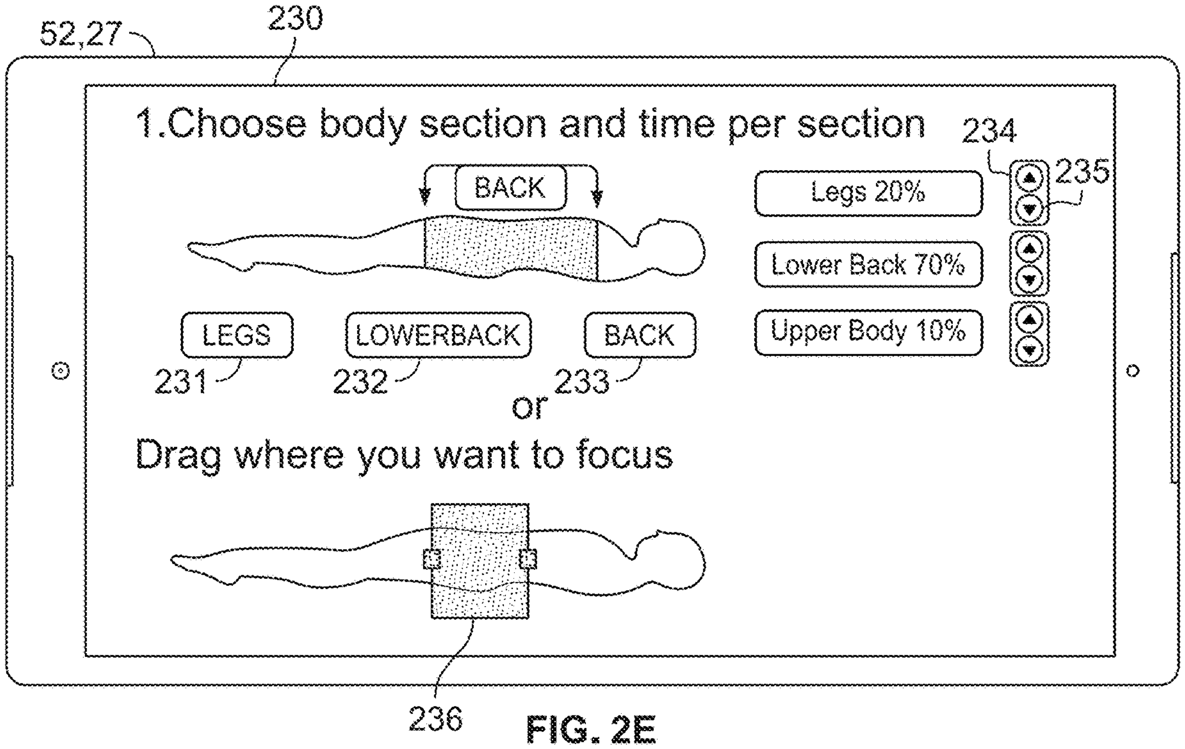

After the user has selected a payment method, another interactive "body section and time" menu 230 is shown in FIG. 2E which allows the user to customize the massage experience. Menu 230 can also be referred to a massage experience page where the user can select icons 231-236 to customize a desired massage experience. In a preferred embodiment, the silhouette of human body is shown on touchscreen 52, 27 wherein the silhouette is divided into three distinct regions: "Legs" 231, "Lower Back" 232, and "Back" 233. As shown in the upper half of the display of touchscreen 52, 27 wherein the user is instructed to "Choose body section and time per section," the user may select each region with the option of choosing the percentage of time each region is massaged, up to 100% total massage time. There are up 234 and down arrows 235 for increasing or decreasing the percentage for each of the identified regions. As an alternative to preselecting the identified regions and percentages of time each of those regions are to be massaged, at the bottom of the menu display shown in FIG. 2E is a drag option 236 to select one region as the focus for the entirety of the massage session, wherein the user is instructed to "Drag where you want to focus."

Figure 2F:
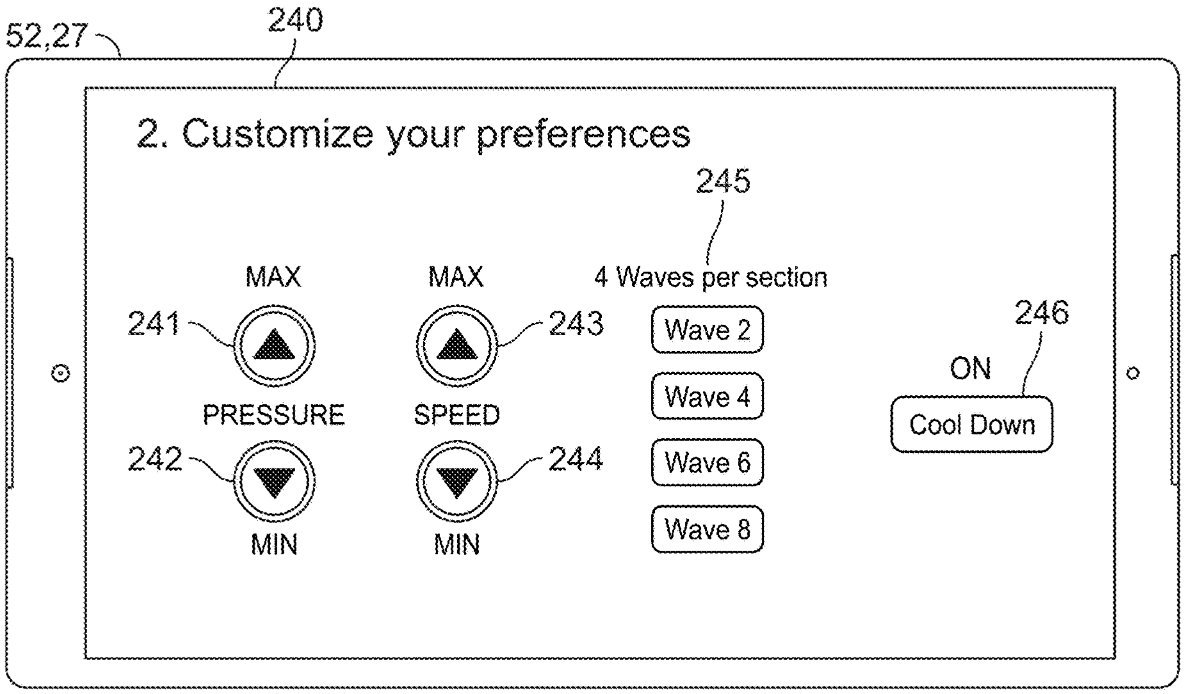

Turning now to FIG. 2F, after selecting the region(s) to be massaged and/or selecting the percentage of massage time for each region if more than one is selected in the "body section and time" menu 230, the user is then presented with a "massage customization" menu 240 which allows the user to further customize the massage experience. Thus, selections made by the user on menu 230 further refine the massage experience set by the user on massage experience page 230. Up arrow 241 and down arrow 242 are provided on touchscreen 52, 27 for the user to customize the pressure of the massage. Also, up arrow 243 and down arrow 244 are present on the "massage customization" menu 240 to adjust the speed generated by the waterjets of dry hydrotherapy massage system 50 during the massage experience. Further options shown therein allow the user to choose the "Waves per section" section 254 with selectable icons as well as a "Cool Down" icon 246. By selecting the icons of pages 230, 240, the user sets the aspects of a desired massage experience. When the user is finished making the selections on pages 230, 240, controller 58 is configured to control water jest system 56 in accordance with the selections made by the user on pages 230, 240 to provide the user the desired massage experience.

Figure 2G:
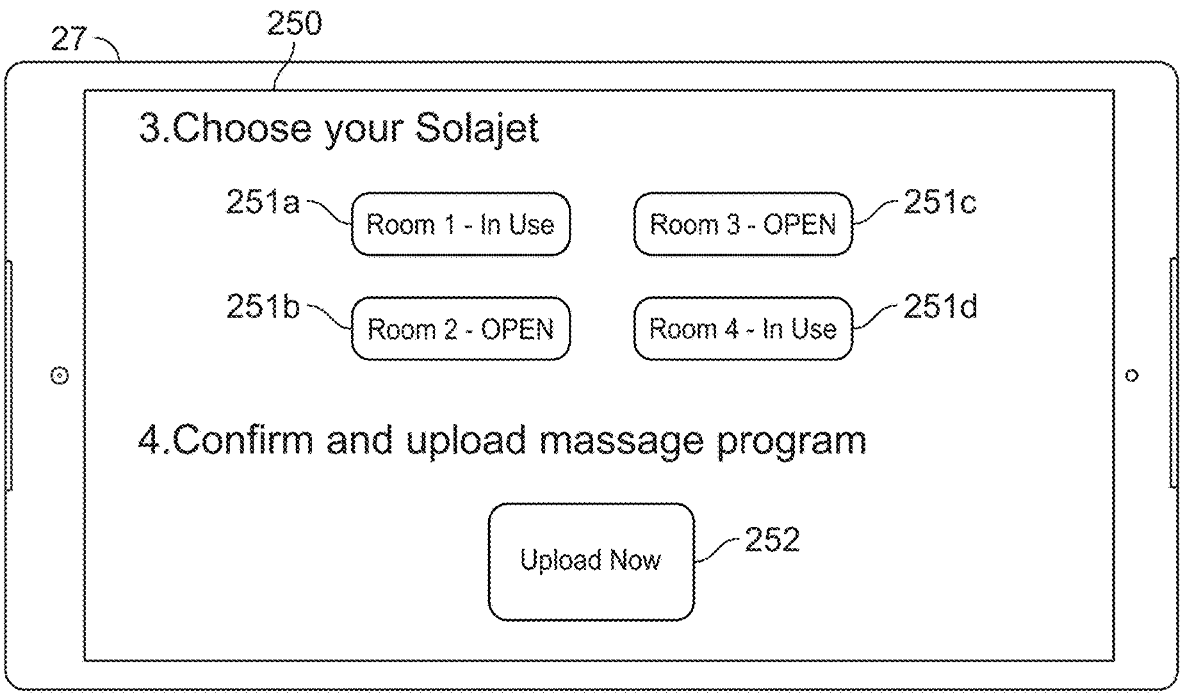

If a user is interacting with touchscreen 27 at a kiosk 25 location within facility 12, the room selection and availability menu page 250 screen shown in FIG. 2G would be presented to the user. As shown at the top of the display of the screenshot of touchscreen 27 in FIG. 2G is the option 251*a-d* for the user to select a particular dry hydrotherapy massage system 50 unit located within an open therapy room 30 of the facility 12. For purposes of example only, there is shown four rooms 30 having dry hydrotherapy massage systems 50 from which to choose. Also indicated as a component of the room choice option is an indication which rooms are available or "Open" (Rooms 2 and 3, as shown), as well as rooms which are not available or "In Use" at the current time (Rooms 1 and 4, as shown). When a room is not currently available for selection, the option to select such a room will be disabled on touchscreen 27. After selecting a currently available room, the user is then instructed to "Confirm and upload massage program" in which any previous customizations selected on previous menu screens are confirmed. Upon pressing the "Upload now" button 252, the user's desired massage experience program is then uploaded to the particular dry hydrotherapy massage system 50 or the room 30 selected by the user.

Figure 2H:
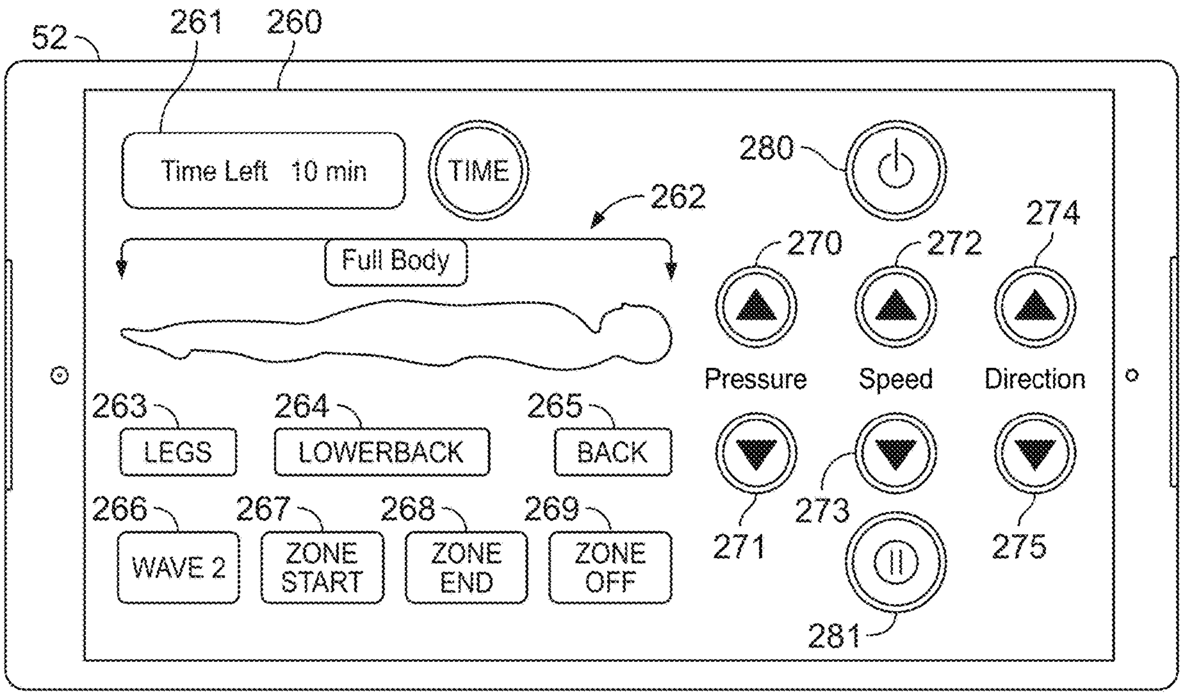

Finally turning to FIG. 2H, there is shown an example of a massage experience status and adjustment page 260 as presented on touchscreen 52. Massage experience page 260 is presented to the user on interface 52 as system 50 is delivering the desired massage experience that was specified by the user based on the selection made on pages 230 and 240, and allows the user to make changes to aspects of the massage experience in real time by selection of the various icons 263-281 of page 260. At the top left of the screen 260, there is a display feature 261 indicating the amount of time left in the current massage treatment. Below the countdown feature is an icon 262 in the shape of a prone human body showing which areas of the body are being massaged, this being "Full Body" in the example provided in FIG. 2H. Below this icon are icons representing the three distinct regions to which dry hydrotherapy massage may be directed ("Legs" 263, "Lower Back" 264, and "Back" 265), as well as icons to modify the massage therapy including icons for starting and ending the massage therapy in a particular zone. Shown in this example, the "Wave" selection 266, "Zone start" 267, "Zone end" 268 and "Zone off" 269 options are presented to the user in an intuitive manner.

As shown on the right side of touchscreen 52 as illustrated in the example of FIG. 2H, there are icons for modifying the massage therapy during the receipt of treatment. For example, there are up arrows and down arrows for increasing or decreasing "Pressure" 270 & 271, "Speed" 272 & 273, and "Direction" 274 & 275 while the dry hydrotherapy massage is in progress. Additionally, above the arrow icons is a power icon 280, and below the arrow icons is an icon for pausing 281 the dry hydrotherapy massage session in while the dry hydrotherapy massage is in progress. Controller 58 is configured to adjust the operation of water jet system 56 based on the selections made by the user on massage experience status page 260. Accordingly, the user can adjust aspects of their desired massage experience in real time using massage experience status page 260.

Although FIGS. 2B-2H illustrate display screens and setting specific to massage therapy, those in with skill in the art will recognize that in various other embodiments of this disclosure analogous screens and settings are displayed to the user of any of the endo-kinetic equipment, devices, and systems disclosed herein. FIGS. 2B-2H are shown as being used with system 50 as a mere illustration of one of the many embodiments of the disclosure.

Figure 3:
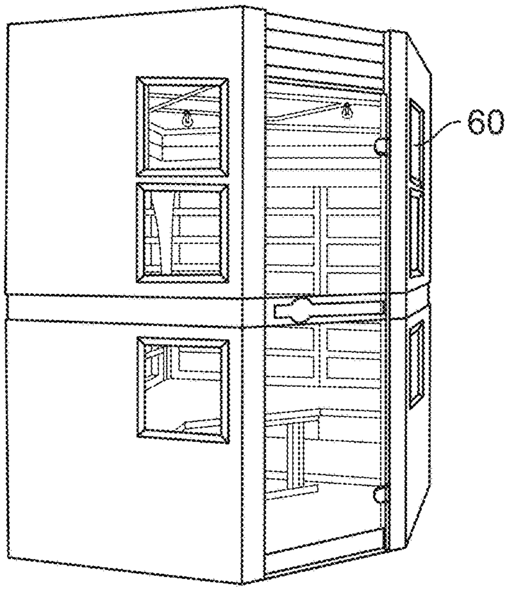
FIG. 3 shows a preferred sauna system for use in a facility as a component of the system disclosed.

Some embodiments of system 10 may also include sauna systems 60, as shown in FIG. 3, which preferably incorporate infrared heaters resulting in nearly zero electromagnetic field (EMF) production. Sauna system 60 could be incorporated into facility 12 in areas such as private therapy rooms 3. Sauna systems 60 in some embodiments of system 10 can provide full spectrum light therapy which mimics the sun's ability to naturally improve mood while eliminating harmful rays. Benefits which may result from the use of the preferred sauna system 60 include, but are not limited to, detoxification, pain relief, improved circulation, weight loss, blood pressure reduction, relaxation, and reduction of inflammation. Infrared sauna systems 60 may include systems like those developed by SunSauna® LLC, which is shown in FIG. 3.

Preferred sauna systems 60 can range in capacity from one person to four or more people. Provided inside the sauna system 60 are seating areas, preferably with seating surfaces which incorporate Microban® and an auto-disinfect feature.

Figure 4:
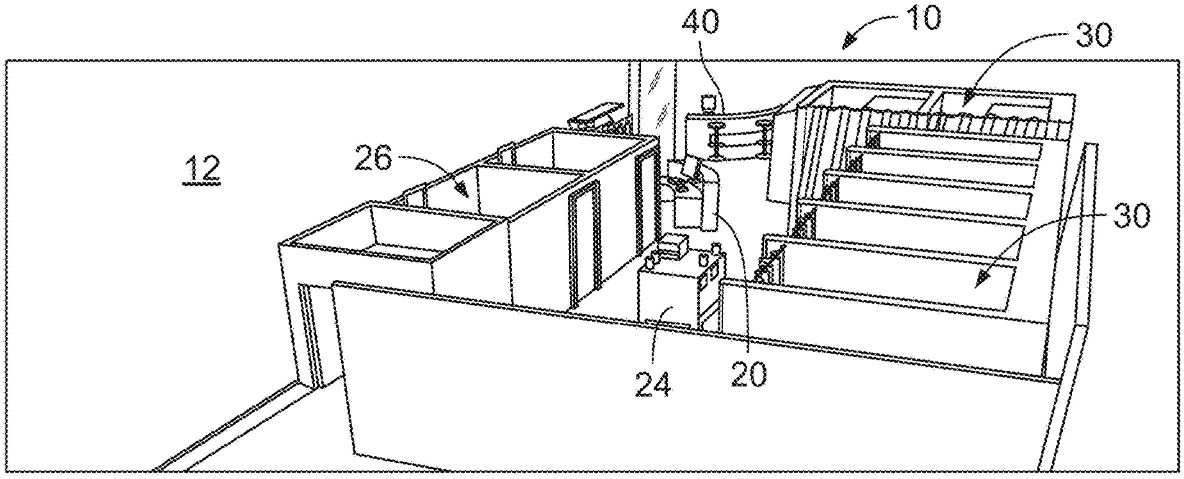
FIG. 4 is an alternate view from that shown in FIG. 1, including showing system elements within the facility.
Figure 6:
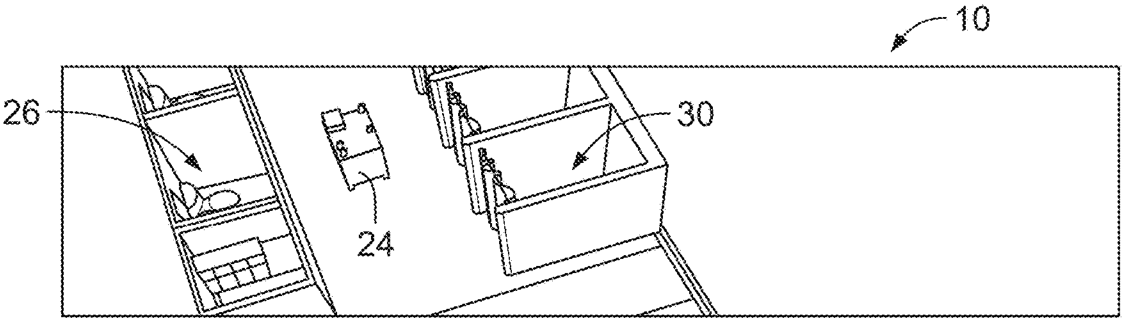
FIG. 6 is an alternate view of the placement of system elements from those of FIG. 1.

Turning now to FIGS. 4 & 6, there are shown alternate views of one embodiment of system 10 showing a particular arrangement of some components of system 10 within facility 12. System components previously described can be seen in the arrangement in facility 12, including beverage station 40, service desk 20, private therapy rooms 30, and technology centers 26. In some preferred embodiments, beverage station 40 may include a "Hydration Station" which is a customizable energy water dispenser to help relax and replenish the body of a user of system 10 after exercise, massage, or other wellness therapies. Also shown in this view are cabinets 24 for storing complimentary items which may be needed by users of system 10, including towels and the like.

Figure 5:
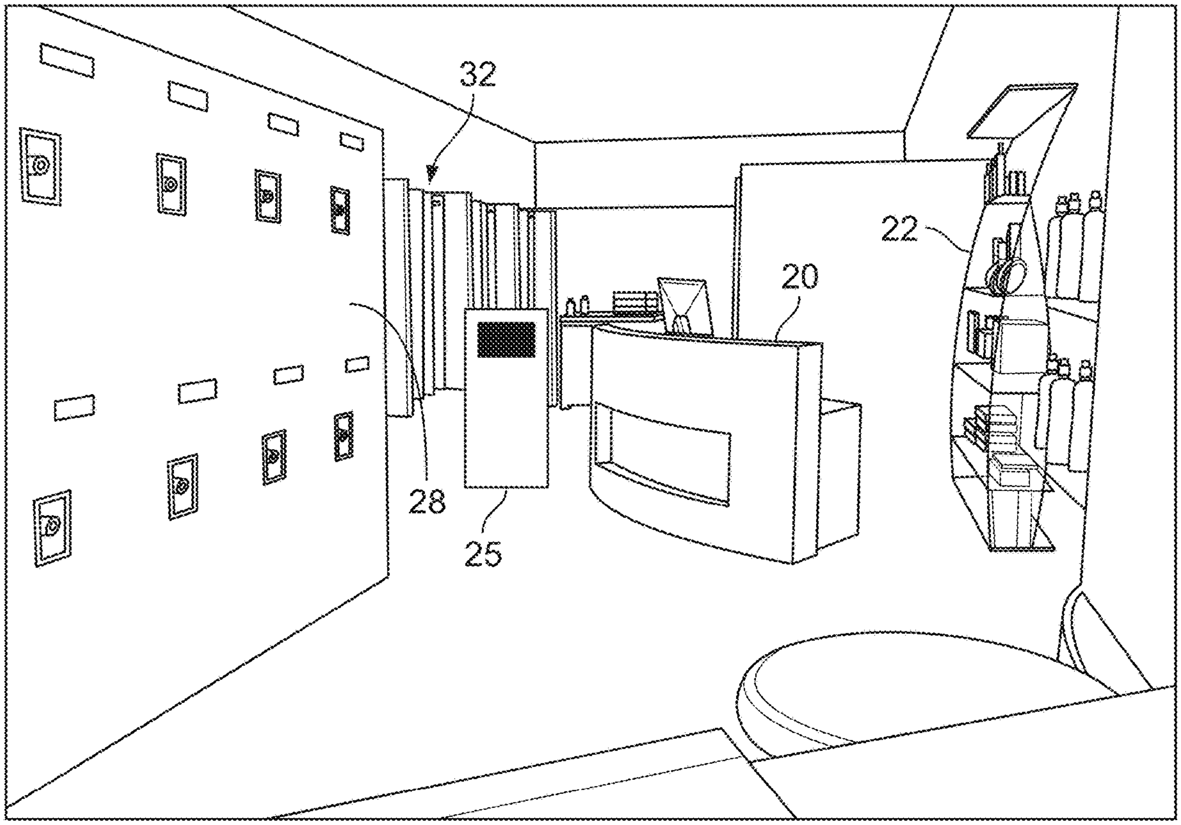
FIG. 5 shows a service desk as well as a product display of a facility of the system disclosed.

An alternate view of service desk 20 is shown in FIG. 5. Also shown is product display 22 which displays various products related to health and wellness available for purchase by member or non-member users of system 10. Across from service desk 20 are storage compartments 28, available for use by members for storing personal items which are not needed or possession of which may in some way hinder the therapy experience of a member while accessing facility 12.

As previously mentioned, preferred embodiments of system 10 incorporate a membership structure in which persons can remit periodic payments for accessing facility 12 and the system components provided therein. An example of a dry hydrotherapy massage membership pricing structure is shown in FIG. 8. This membership pricing schedule, more particularly the amount for each service or membership tier provided in FIG. 8, is merely an example, and is not intended to limit the scope of the present invention. Those of skill in the art will understand that any number of pricing and service combinations could be utilized in the context of system 10 as described herein.

As can be seen in the chart illustrated in FIG. 8, membership structure may be in a tiered system, both in relation to price and services provided. This example shows a monthly payment period for membership; however, other periods could be implemented, including weekly, bi-monthly, semi-annually, annually, etc.

Along the top row are listed possible membership tiers including Premium, Express, and Massage Membership. Each membership tier includes the number of massage sessions which are included in the monthly price.

As is also shown in the chart, access to facility 12, and more particularly the services provided as incorporated into system 10, differs between each of the membership tier options. A person paying for a Premium Membership would have unlimited access to dry hydrotherapy massage sessions. According to this example, the periodic payment (on a monthly basis in the example) would be the highest for the Premium Membership tier, which affords a customer the most access to the services provided.

The Express (mid-level tier) membership would have a lower monthly fee but would also result in more limited access to the services provided. As in the example illustrated in FIG. 8, a person paying for the Express Membership would only have access to ten (10) dry hydrotherapy massage sessions as compared to unlimited access accorded to those paying for a Premium Membership.

Also shown is a Massage Membership tier in which only five (5) dry hydrotherapy massage sessions would be available. This would be the lowest priced membership tier, and accordingly would be afforded the least amount of access to the dry hydrotherapy massage services.

It is further anticipated that alternative embodiments may provide options for an a la carte payment method. Payment would be on a per-service or per-access basis, each and every time a person sought such service or access. It is contemplated that prices for individual services would be higher than comparable services under the membership tiers available.

Again, the chart illustrated in FIG. 8 is merely one example of a possible structuring mechanism for membership pricing for providing access to facility 12 and the services and products incorporated into system 10. Many other membership structures could be offered within the scope of the present invention herein described as would be understood by one of ordinary skill in the art. It is also contemplated that access to other health and wellness services may be included in the tiered membership structure, and prices for such memberships as well as access to such services would be determined accordingly.

Figure 10A:
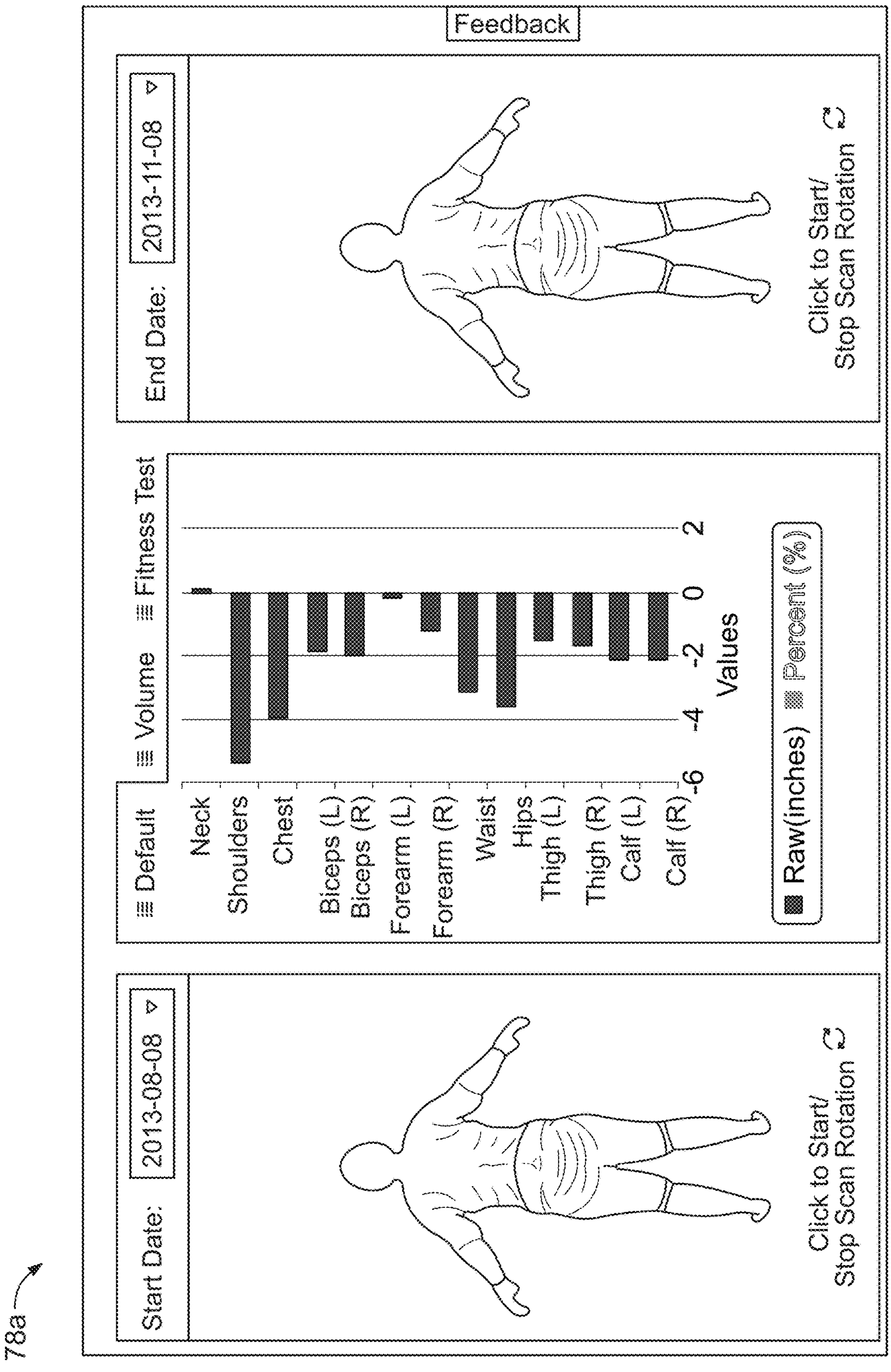
FIGS. 10A & 10B illustrate the output produced by the body analyzer of FIG. 9.
Figure 10B:
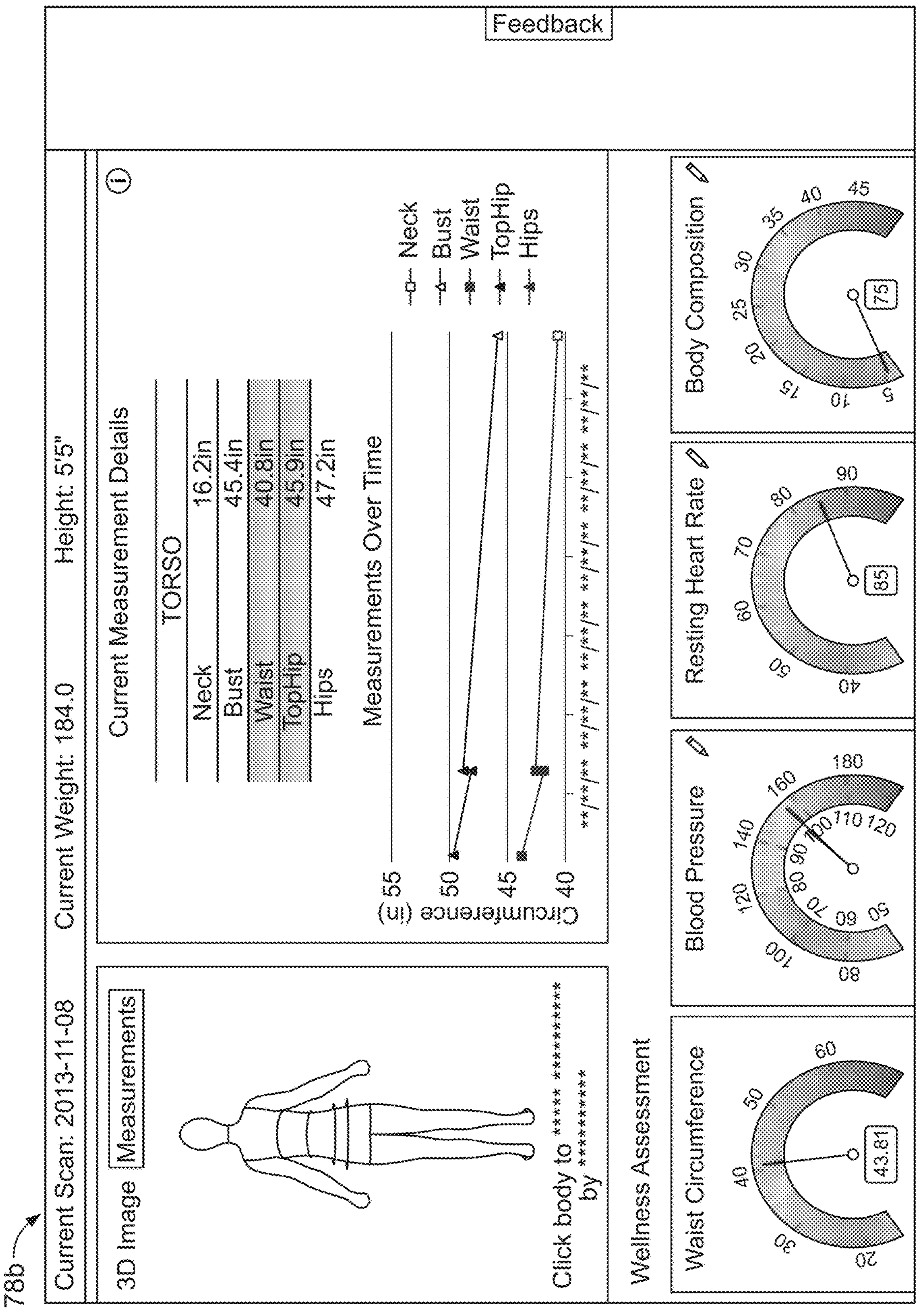

In alternative embodiments of the presently disclosed system 10 may include other accessory health and wellness services, including but not limited to, body analyzers and various exercise equipment. For instance, FIG. 9 shows one type of apparatus for performing body analysis. More particularly, the model shown in FIG. 9 is "The Personal Avatar" or body analyzer 76 which is a highly accurate three-dimensional (3-D) external body mapping system. This particular system provides detailed body measurements and software to record and track changes and personal progress of an individual over time. FIGS. 10A & 10B show two examples of an output produced by the body mapping system indicating some of the detailed information which the body mapping system is capable of providing to the user. These screenshots 78*a* & 78*b* are representative of the outputs which can be viewed and analyzed online at the web address "www.fit3d.com."

Figure 11A:
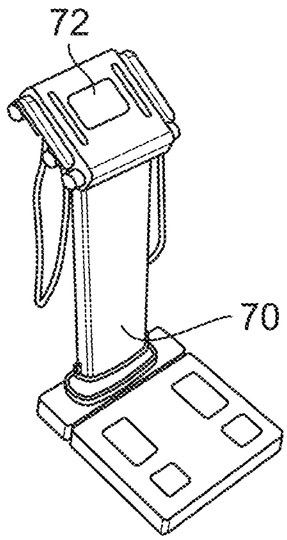
FIGS. 11A & 11B illustrate a possible component of alternative embodiments of the system disclosed being a body analyzer and the output produced by the body analyzer as shown on a display screen.
Figure 11B:
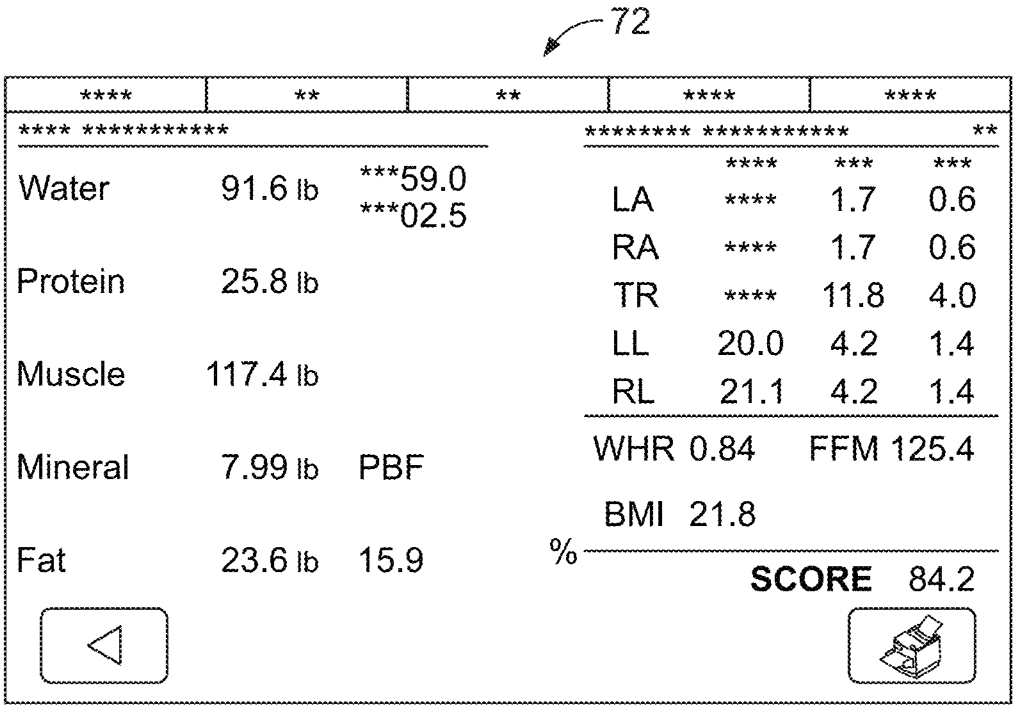

Another component which may be incorporated into alternative embodiments of the presently disclosed system 10 as an accessory is shown in the photographs represented in FIGS. 11A & 11B. A bioimpedance-based body analyzer 70, also referred to as "The Body Compass™," is shown in FIG. 11A, and can provide a technology-based body analysis. More particularly, body analyzer 70 can provide core baseline measurements of density and/or percentage of hydration, muscle, bone, fat, and mineral. Output produced by body analyzer 70 is displayed on output screen 72, a close-up photograph of output screen 72 being shown in FIG. 11B. Bioimpedance-based body analysis is an emerging technology being adapted by leading physicians, chiropractors and wellness providers.

Possible integrations with body analysis are applications (or "apps"), with an example being a body planner app (not shown) which can allow a user to organize and manage a personal development plan ranging from strength training, diet and nutrition, as well as flexibility and the like. Another such app which can be provided in this context includes a nutrition application 74, such as is shown in FIG. 7. Nutrition application 74 is capable of providing ready access to important nutrition data and tools to assist with planning a diet based on the needs of a particular user in accordance with previously performed body analysis. These applications can generally be accessed or used on portable computing devices such as smartphones, tablets, and the like. Other applications are contemplated which relate to fitness, diet, or other such concepts associated with health and wells, as would be readily understood by those of ordinary skill in the art.

Figure 12A:
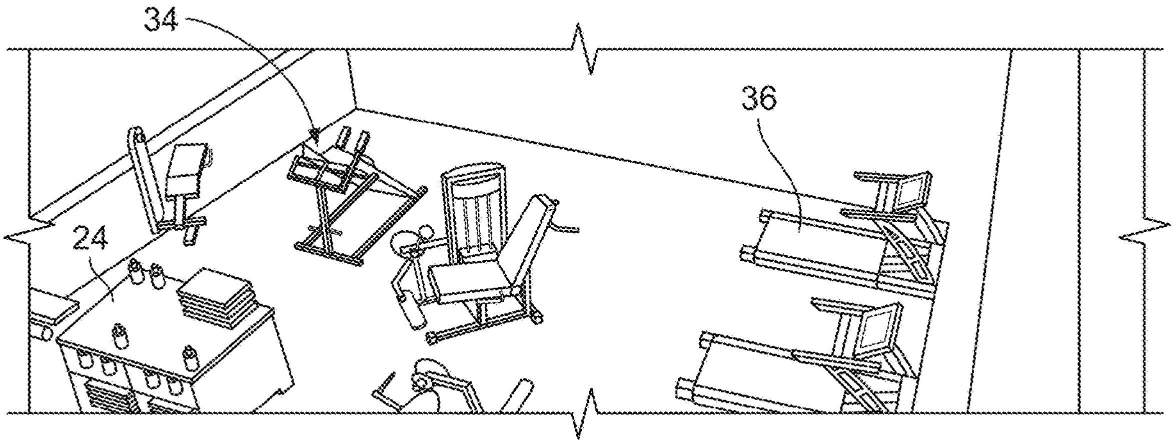
FIGS. 12A & 12B illustrate potential additional components offered as part of alternative embodiments of the system disclosed.
Figure 12B:
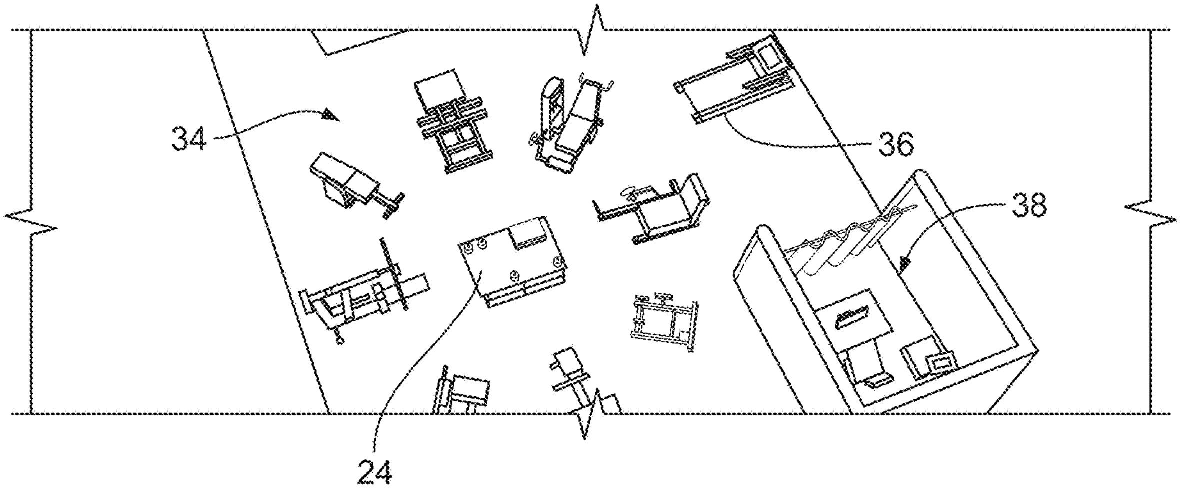

It is also contemplated that other accessory health and wellness products and services may be provided in alternative embodiments of system 10. For example, facility 12 may also include a circuit training center 34 as shown in FIGS. 12A & 12B. Incorporated in circuit training center 34 are various exercise machines and equipment including treadmill 36.

Figure 13:
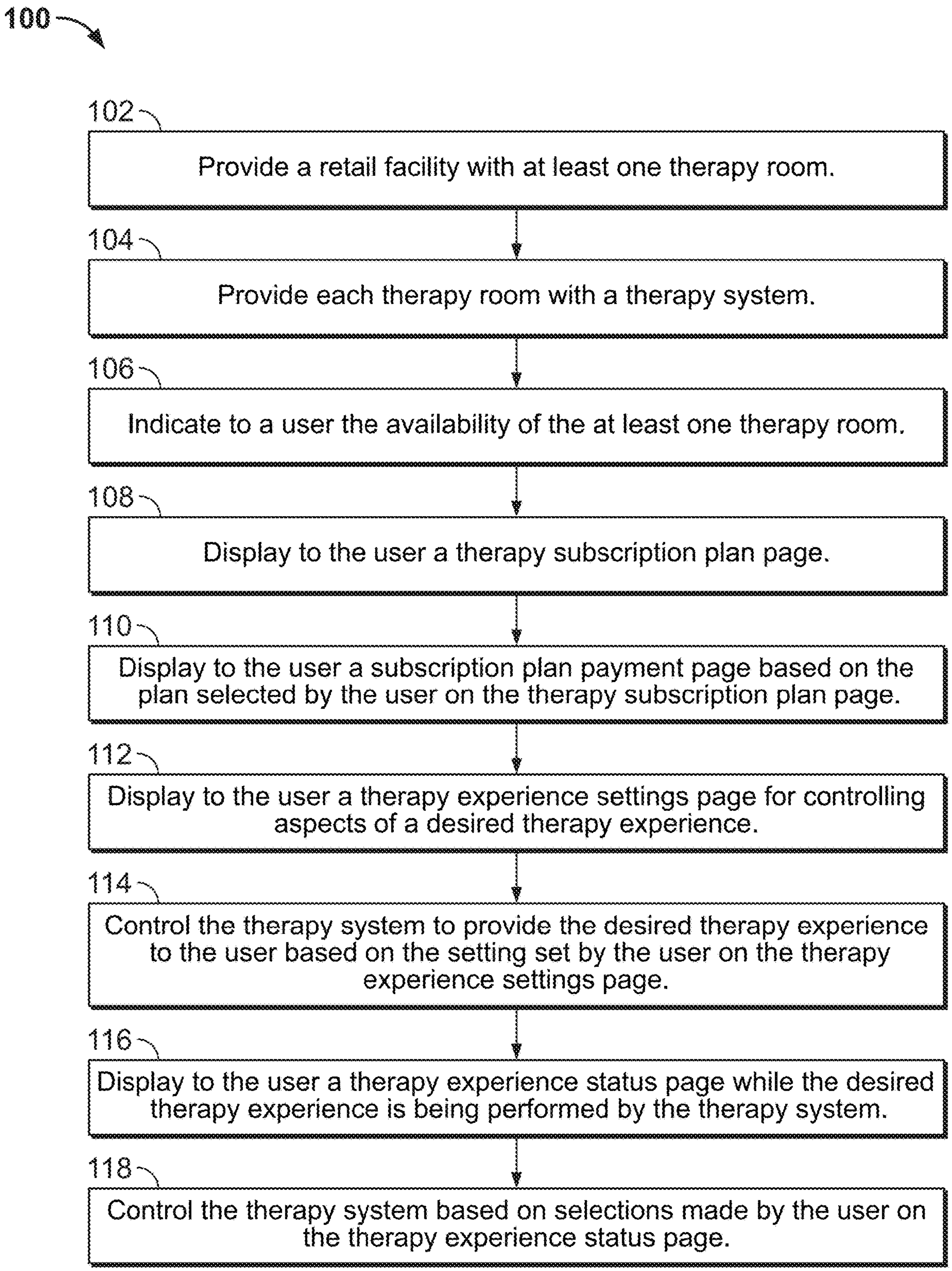
FIG. 13 is a flowchart illustrating a method of providing a subscription-based physical therapy experience to a user, according to an embodiment of this disclosure.

FIG. 13 is flowchart illustrating a method 100 of providing a subscription-based endo-kinetic physical therapy experience to a user. Method 13 can begin at block 102 providing a retail facility 12 with at least one therapy room 30. Method 100 can continue at block 104 by providing each therapy room 30 with a therapy system, such as, for example, hydrotherapy system 50. Method 100 can optionally continue at block 106 by indication to the user the availability of therapy rooms 30. For example, in some embodiment, check-in kiosk 25 can display to the user availability of therapy rooms 30 on room availability page 250, as previously discussed.

Method 100 can continue at block 108 by displaying subscription plan page 210 to the user. In some embodiments, subscription plan page 210 is displayed on the graphical user interface 52 of the hydrotherapy table system 50. In some embodiments, subscription plan page 210 is displayed on the graphical user interface 27 of the check-in kiosk 25.

In response to the user selecting a subscription plan option 211, 212, 213, 214 of the subscription plan payment page 210, method 100 can continue at block 110 by displaying a subscription plan payment page 220 with payment instructions for the subscription plan option 211, 212, 213, 214 selected by the user. In some embodiments, subscription plan payment page 220 is displayed on the graphical user interface 52 of the hydrotherapy table system 50. In some embodiments, subscription plan payment page 220 is displayed on the graphical user interface 27 of the check-in kiosk 25.

Method 100 can continue at block 112 by displaying to the user massage experience setting page 230 so that the user can set aspects of a desired massage experience. In some embodiments, massage experience settings page 230 is displayed on the graphical user interface 52 of the hydrotherapy table system 50. In some embodiments, massage experience settings page 230 is displayed on the graphical user interface 27 of check-in kiosk 25. In some embodiments, block 112 includes displaying to the user customization page 240 to further refine the massage aspects selected by the user on page 230.

Method 100 can continue at block 114 by performing the desired massage experience based on the inputs made by the user in block 112. Specifically, control system 58 controls water jet system 56 to provide the user with the desired massage experience based on setting input by the user on the massage experience settings pages 230 and 240.

Method 100 can optionally continue at block 116 displaying to the user massage experience status page 260 to user while massage therapy table 50 is performing the desired massage experience specified by the user by the selections made on pages 230 and 240. Massage experience status page 260 is displayed to user on the graphical user interface 52 of the massage table system 52 so that the user can view the status information of their massage experience in real-time and make changes to the massage experience in real-time.

Method 100 can continue at block 118 by controlling the hydrotherapy massage table 50 based on inputs made by the user in block 116. Specifically, control system 58 can control water jet system 56 based on inputs made by the user on the graphical user interface 52 massage experience status page 260. As an illustrative example, the control system 58 may detect that the user has selected icon 270 of massage experience status page 260 to increase the pressure of the desired massage experience. In response to this, the control system 58 controls water jet system 56 to increase the water pressure directed at the user platform 54 to increase the pressure of the desired massage experience, in accordance with the selections made by the user on the massage experience status page 260.

As has been described above, method 100 can utilize either of or both of graphical user interface 52 of massage system 50 and graphical user interface 27 of check-in kiosk 25. For example, in some embodiments, method 100 first utilizes check-in kiosk 25. When a user enters facility 12, blocks 106-114 are performed using graphical user interface 27 at kiosk 25 before the user enters the therapy room 30. That is to say, in some embodiments, the user checks room availability, selects a subscription plan, selects a payment option for the plan, and sets aspects of a desired massage experience at kiosk 25, and kiosk 25 then communicates the aspects of the desired massage experience to the control system 58 of the massage system 50 of the therapy room 30 selected by the user in block 106. The user can then enter the selected therapy room 30 to receive the massage experience from system 50 that was specified at the kiosk 25. While the desired massage experience is being performed by the system 50, blocks 116-118 can be performed by graphical user interface 52, where appropriate, to modify the desired massage experience in real-time.

In other embodiments, kiosk 25 is only used to indicate availability of rooms in block 106, and blocks 108-118 are performed using graphical user interface 52, where appropriate. In other embodiments, method 100 is performed without the use of kiosk 25. Indication of available rooms 30 in block 106 can be performed by any of a number of other methods, such as, for example, availability lights or signals in communication with associated massage systems 50 that indicate to the user whether the therapy room 30 is occupied or available for use, and blocks 108-118 are performed using graphical user interface 52, where appropriate. Those with skill in the art will understand there are still many different combinations in which graphical user interface 27 and graphical user interface 52 can be used together, where appropriate, to practice method 100.

Although method 100 illustrates blocks 102-118 occurring in a certain order, method 100 can be practiced by performing blocks 102-118 in any of a number of orders. For example, in some embodiments, some or all of blocks 106-110 of indicating room availability, displaying subscription options, and displaying payment page are displayed after the user has selected the aspects of their desired massage experience in block 112. Additionally, in some embodiments, method 100 is practiced without utilizing certain blocks 102-118. In some embodiments, method 100 is practiced using additional steps.

Figure 14:
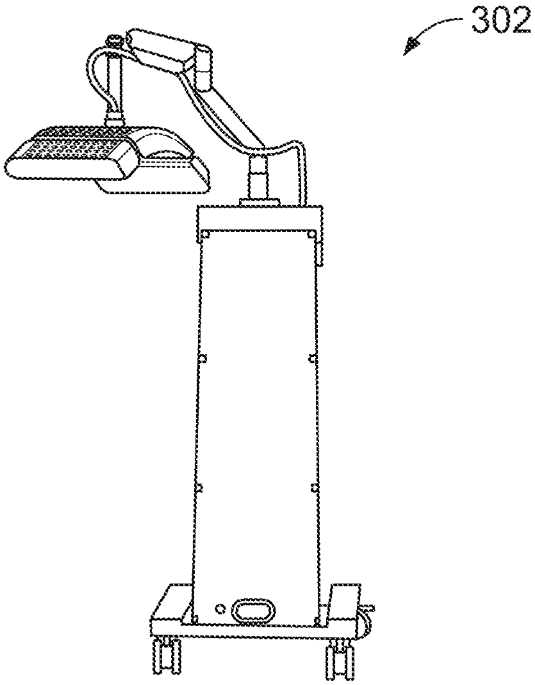
FIG. 14 illustrates a LED light therapy of the system disclosed.
Figure 15:
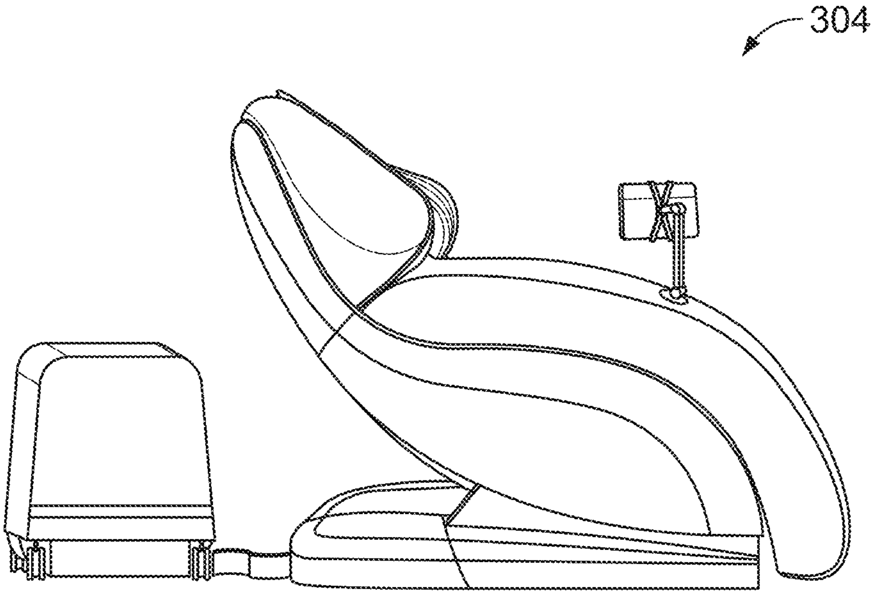
FIG. 15 illustrates a massage chair of the system disclosed.
Figure 16:
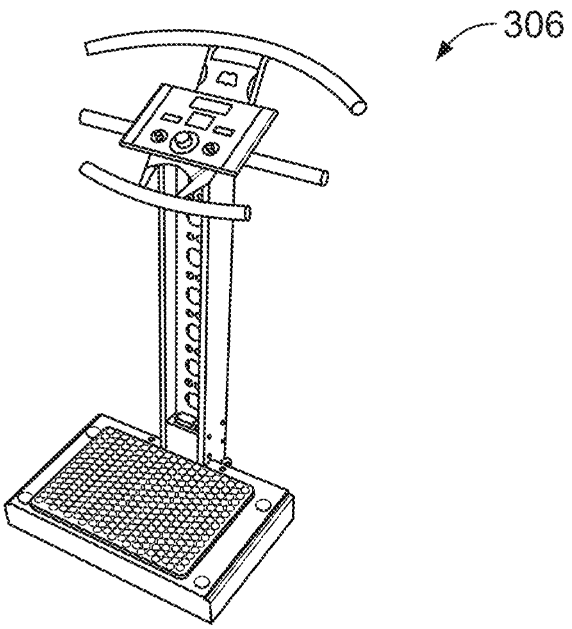
FIG. 16 illustrates body vibration machine of the system disclosed.
Figure 17:
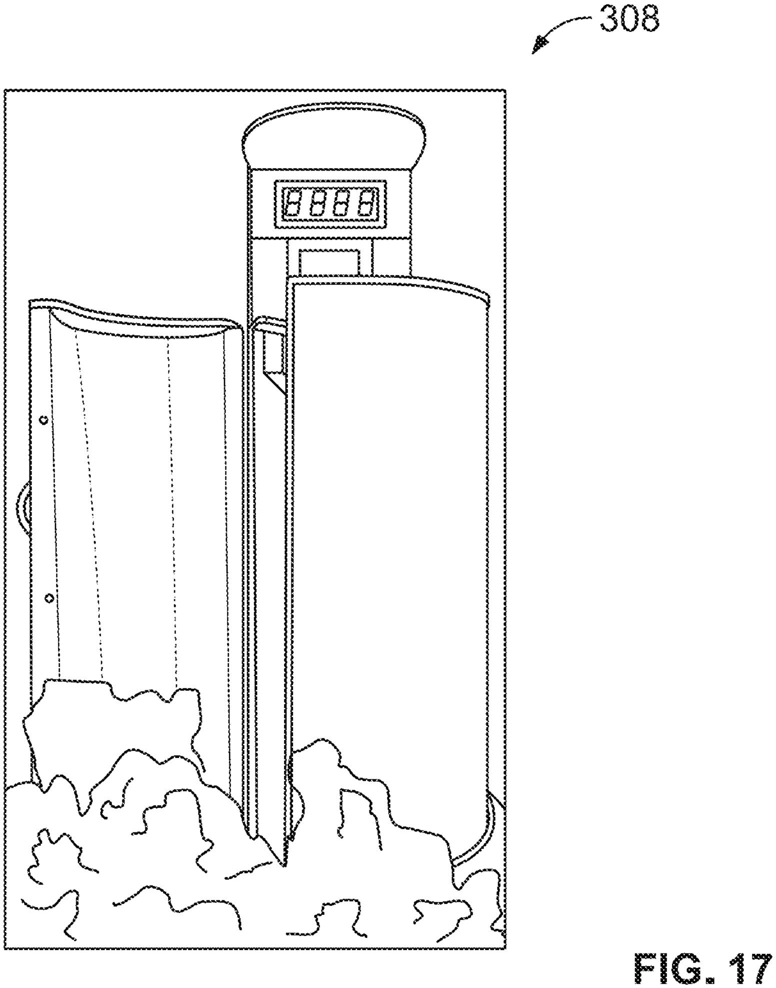
FIG. 17 illustrates a cryochamber of the system disclosed.
Figure 18:
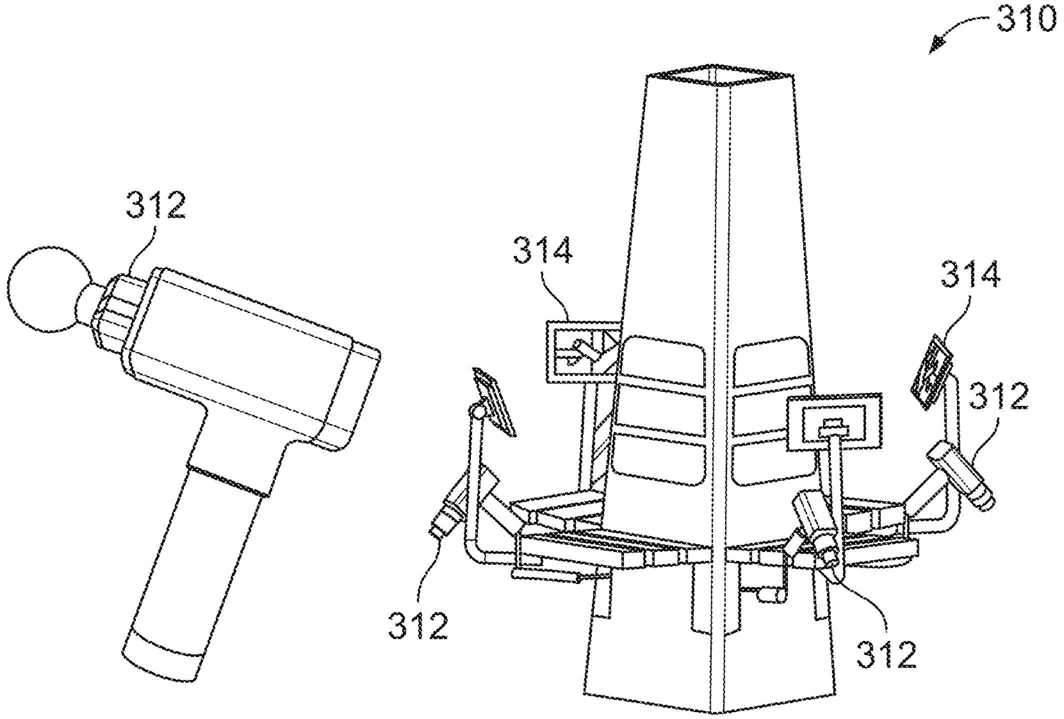
FIG. 18 illustrates a percussive therapeutic gun station of the system disclosed.
Figure 19:
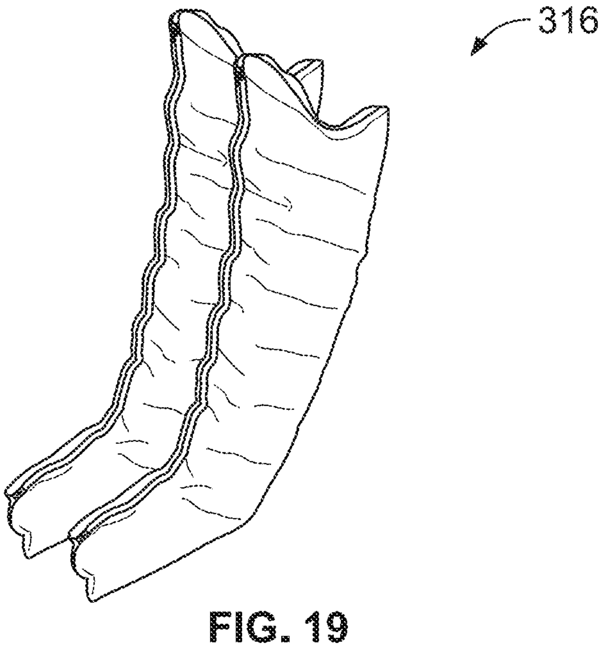
FIG. 19 illustrates massage extremity sleeves of the system disclosed.

Although method 100 describes a method for offering a subscription-based service for Endo-Kinetic treatment hydrotherapy massages using a hydrotherapy massage table 50, one with skill in the art will understand that other types of procedures, therapies, and endo-kinetic treatments can be included in the subscription-based therapy service of method 100. Method 100 can be practiced using any of the endo-kinetic systems and devices disclosed herein. For example, in some embodiments, instead of or in addition to offering hydrotherapy massages with massage system 50, method 100 can include offering dermatological therapies using a LED light therapy machine 302 illustrated in FIG. 14. In some embodiments, instead of or in addition to offering the hydrotherapy massages using table 50, method 100 can include offering massages using endo-kinetic massaging chair 304 illustrated in FIG. 15. In some embodiments, massaging chair can be a hydrotherapy chair, such as the hydrotherapy chairs described in U.S. patent application Ser. No. 16/905,564 and U.S. provisional application No. 63/278,256. U.S. patent application Ser. No. 16/905,564 and U.S. provisional application No. 63/278,256 are incorporated by reference in their entireties. In some embodiments, endo-kinetic treatments of method 100 can include offering body vibration therapy with full body vibration machine 306 illustrated in FIG. 16. In some embodiments, endo-kinetic treatments of method 100 includes offering cryotherapy using cryotherapy chamber 308 illustrated in FIG. 17. In some embodiments, endo-kinetic treatments of method 100 can include offering heat therapy using sauna 60 illustrated in FIG. 3. In some embodiments, endo-kinetic treatments of method 100 can include offering self-service massage therapy with percussive gun station 310 illustrated in FIG. 18. Station 310 has a plurality of percussive handheld massaging guns 312 and a plurality of graphical user interfaces 314 associated with each of the plurality massaging guns 312. Graphical user interfaces 314 are substantially the same as graphical user interfaces 52. In some embodiments, endo-kinetic treatments of method 100 can includes offering self-service massage therapy using extremity compressions sleeves 316 illustrated in FIG. 19. Accordingly, those will skill in the art will recognize that in various embodiments of this disclosure, method 100 is applied to any of the endo-kinetic devices and systems described herein. Method 100 is described refencing system 50 as a mere illustration of one of the many embodiments of this disclosure in which method 100 is performed using any of the endo-kinetic systems described herein.

This is to say, the embodiments of this disclosure are not limited to subscription-based service for offering massage therapies. One with skill in the art will understand that in other embodiments of the disclosure, the subscription-based methods described are applied to any of the therapies, procedures and endo-kinetic treatments disclosed herein. Specifically, according to some embodiments, the therapies and procedures offered under the subscription-based methods described require little to no direct interaction by operators or employees of the retail facility 12. As described in method 100, a user can enter retail facility 12 and receive a hydrotherapy massage without interacting with an employee of the retail facility or a masseuse. Similarly, in some embodiments, method 100 can be incorporated with LED light therapy machine 302, massaging chair 304, vibration machine 306, sauna 60, hydrotherapy chamber 308, percussive gun station 310, and/or extremity compressions sleeves 316 without interacting an employee of retail facility 12.

However, in other embodiments, method 100 can be incorporated with therapies or procedures that involve interaction with a professional. For example, in some embodiments, the subscription-based methods described in method 100 can be used to schedule: massage details with a masseuse; massage details with a health professional operating a hand-held massaging device; cryotherapy with a professional operating a handheld cryotherapy device; or a stretching/flexibility session with a professional.

Some embodiments of the disclosure include using method 100 to offer users access to any of a number of therapy devices within facility 12. For example, in some embodiments, a user's subscription to the facility allows the user access to any of the therapy equipment disclosed herein, such as hydrotherapy massage system 50, sauna 60, LED light therapy machine 302, massage chair 304, body vibration machine 306, cryotherapy machine 308, percussive gun station 310, and extremity compression sleeves 316.

FIGS. 20A and 20B illustrate an embodiment of the disclosure in which a point system is used in the subscription-based service disclosed. For example, as illustrated in FIG. 20A, a user may purchase a monthly care package ranging from an Express Package in which the user purchases 5 points a month, to an Ultimate Package in which the purchases 60 points a month. Each point can be used to redeem a session with one of the endo-kinetic therapy systems (such as, for example, hydrotherapy massage system 50, sauna 60, LED light therapy machine 302, massage chair 304, body vibration machine 306, cryotherapy machine 308, percussive gun station 310, and extremity compression sleeves 316) offered by the facility 12. Additionally, a user can purchase a point care pack, illustrated in FIG. 20B, without having to subscribe to a monthly plan. Those with skill in the art will recognize that point-based subscription options, like those presented in FIGS. 20A and 20B, can be displayed as selectable icons to the user on graphical user interface 52, 27 on subscription plan page 210 previously discussed. Thus, method 100 can utilize the point system to offer any of a number of endo-kinetic therapies to a user with a subscription plan or a care pack.

The figures and descriptions in this application depict specific examples to teach those skilled in the art how to make and use the best mode of the invention. These examples are not given to limit the scope of the invention, but rather to teach inventive principles. To concisely teach inventive principles, some conventional aspects of the invention have been simplified or omitted. Those skilled in the art will appreciate many of the configurations, combinations, subcombinations, and variations on these examples that fall within the scope of the invention. For example, certain features of the invention described in separate embodiments can also be implemented in combination in a single embodiment. Conversely, various features that are described in the context of a single embodiment can also be implemented in multiple embodiments-separately or in any suitable subcombination. The invention is not limited to the specific illustrative examples described herein, but by all embodiments and methods within the scope and spirit of the invention as in the current, amended, or added claims and their equivalents. In any case, all substantially equivalent systems, articles, and methods should be considered within the scope of the invention.

What is claimed is:

1. A method of providing a massage experience to a user in a retail facility using a subscription-based service, the method comprising:

providing the retail facility with a plurality of therapy rooms;

providing each therapy room of the plurality of therapy rooms with a hydrotherapy massage system, each hydrotherapy massage system including:

a massaging platform having an outer surface upon which the user sits or lies to receive the massage experience, a water jet system configured to expel water against an inside surface of the massaging platform to provide the user with the massage experience, and a control system configured to control operation of the water jet system;

providing a first graphical user interface configured to communicate with the control system, wherein the control system is configured to operate the water jet system based on inputs received at the first graphical user interface;

displaying to the user, via the first graphical user interface, a subscription plan page including a plurality of selectable subscription plan options, each of the plurality of subscription plan options describing details of the associated subscription plan, wherein the details include a price of the subscription plan for a plan period, a number of massage experiences included within the plan period, and a point system that is associated with the subscription plan;

in response to the user selecting a subscription plan option of the plurality of subscription plan options, displaying to the user, via the first graphical user interface, a subscription plan payment page, the subscription plan payment page including instructions for paying for the subscription plan selected by the user on the subscription plan page;

displaying to the user, via the first graphical user interface, a massage experience settings page including a plurality of selectable icons for programming aspects of a desired massage experience, wherein the said programming aspects include body areas of focus, massage time, massage pressure generated by the water jet system, massage speed generated by the water jet system, and number of waves generated by the water jet system per body area of focus;

in response to selecting a massage time option for each body area of focus, displaying to the user, via the graphical user interface, the percentage of total massage time the user selected for each body area of focus;

displaying to the user, via the first graphical user interface, the availability status information of each therapy room of the plurality of therapy rooms based on communication with the control system of each therapy room of the plurality of therapy rooms;

uploading to the control system, via the first graphical user interface, the selections made by the user on the massage experience settings page to perform the desired massage experience; and controlling water jets, via the control system, based on the selections made by the user on the massage experience settings page to perform the desired massage experience.

2. The method of claim 1, further comprising:

providing a second graphical user interface in each therapy room of the plurality of therapy rooms such that the user can view and interact with the second graphical user interface while the desired massage experience is being performed;

displaying to the user, via the second graphical user interface, a massage experience status page while the desired massage experience is being performed, the massage experience status page including massage status information and the plurality of selectable icons for adjusting aspects of the desired massage experience while the desired massage experience is being performed, wherein the massage status information includes time remaining for the desired massage experience, and wherein the aspects of the desired massage experience associated with the selectable icons for adjusting aspects of the desired massage experience while the desired massage experience is being performed include the body areas of focus, the massage pressure generated by the water jet system, the massage speed generated by the water jet system, the number of waves generated by the water jet system per body area of focus, and a massage direction of the water expelled by the water jet system; and controlling the water jets, via the control system, based on selections made by the user on the massage experience status page for adjusting aspects of the desired massage experience while the desired massage experience is being performed.

3. The method of claim 2, further comprising, in response to one of the plurality of selectable icons being selected by the user on the massage experience status page, adjusting the water jets while the desired massage experience is in progress, via the control system, in accordance with the one of the plurality of selectable icons for adjusting aspects of the desired massage experience selected by the user.

4. The method of claim 1, wherein:

the displaying to the user the availability status information of each therapy room of the plurality of therapy rooms is achieved by a check-in kiosk of the retail facility, the check-in kiosk including the first graphical user interface configured to communicate with the control system of the hydrotherapy massage system of each therapy room of the plurality of therapy rooms.

5. The method of claim 1, wherein the massage experience settings page further comprises a silhouette of a human body, wherein the silhouette is divided into three regions wherein the user may customize the desired massage experience for each region, wherein the user may adjust a percentage of the massage time for each region to be massaged, the massage pressure generated by the water jet system for each region to be massaged, the massage speed generated by the water jet system for each region to be massaged, and the number of waves generated by the water jet system for each region to be massaged.

6. The method of claim 5, wherein the three regions comprise a legs region, a lower back region, and a back region.

7. A method of providing a massage experience to a user in a retail facility using a subscription-based service, the method comprising:

providing the retail facility with at least one therapy room;

providing the at least one therapy room with a hydrotherapy massage system, each hydrotherapy massage system including:

a massaging platform having an outer surface upon which the user sits or lies to receive the massage experience, a water jet system configured to expel water against an inside surface of the massaging platform to provide the user with the massage experience, and a control system configured to control operation of the water jet system;

providing a first graphical user interface configured to communicate with the control system, wherein the control system is configured to operate the water jet system based on inputs received at the first graphical user interface;

displaying to the user, via the first graphical user interface, a subscription plan page including a plurality of selectable subscription plan options, each of the plurality of subscription plan options describing details of the associated subscription plan, wherein the details include a price of the subscription plan for a plan period, a number of massage experiences included within the plan period, and a point system that is associated with the subscription plan;

in response to the user selecting a subscription plan option of the plurality of subscription plan options, displaying to the user, via the first graphical user interface, a subscription plan payment page, the subscription plan payment page including instructions for paying for the subscription plan selected by the user on the subscription plan page;

displaying to the user, via the first graphical user interface, a massage experience settings page including a plurality of selectable icons for controlling aspects of a desired massage experience, wherein the massage experience settings page comprises a silhouette of a human body, wherein the silhouette is divided into three regions wherein the user may customize the desired massage experience for each region, wherein the user may adjust for each region a percentage of time to be massaged, an amount of pressure generated by the water jet system, a speed generated by the water jet system, and a number of waves generated by the water jet system;

in response to the user adjusting the percentage of time to be massaged for each region, displaying to the user, via the graphical user interface, the percentage of total massage time each region is set to;

displaying to the user, via the first graphical user interface, the availability status of the at least one therapy room of the plurality of therapy rooms based on communication with the control system of the at least one therapy room;

uploading to the control system of the at least one therapy room, via the first graphical user interface, the selections made by the user on the massage experience settings page to perform the desired massage experience; and controlling water jets, via the control system, based on selections made by the user on the massage experience settings page to perform the desired massage experience;

providing a second graphical user interface in the at least one therapy room such that the user can view and interact with the second graphical user interface while the desired massage experience is being performed, wherein the second graphical user interface is configured to communicate with the control system of the at least one therapy room, wherein the control system is configured to operate the water jet system based on inputs received at the second graphical user interface;

displaying to the user, via the second graphical user interface, a massage experience adjustment page for the user to modify the desired massage experience while the desired massage experience is being performed, the massage experience adjustment page comprising:

massage status information, wherein said massage status information includes time remaining for the desired massage experience, and a plurality of selectable icons for modifying aspects of the desired massage experience, wherein said modifying aspects include the region being massaged, the pressure generated by the water jet system, the speed generated by the water jet system, the number of waves generated by the water jet system, and a direction of the water expelled by the water jet system, and controlling the water jets, via the control system, based on selections made by the user on the massage experience adjustment page to adjust the desired massage experience while the desired massage experience is being performed.

8. A method of providing a massage experience to a user in a retail facility using a subscription-based service, the method comprising:

providing the retail facility with a plurality of therapy rooms;

providing each therapy room of the plurality of therapy rooms with a hydrotherapy massage system, each hydrotherapy massage system including:

a massaging platform having an outer surface upon which the user sits or lies to receive the massage experience, a water jet system configured to expel water against an inside surface of the massaging platform to provide the user with the massage experience, and a control system configured to control operation of the water jet system;

providing a first graphical user interface configured to communicate with the control system of each therapy room of the plurality of therapy rooms, wherein the control system is configured to operate the water jet system based on inputs received at the first graphical user interface;

displaying to the user, via the first graphical user interface, a subscription plan page including a plurality of selectable subscription plan options, each of the plurality of subscription plan options describing details of the associated subscription plan, wherein the details include a price of the subscription plan for a plan period, a number of massage experiences included within the plan period, and a point system that is associated with the subscription plan;

in response to the user selecting a subscription plan option of the plurality of subscription plan options, displaying to the user, via the first graphical user interface, a subscription plan payment page, the subscription plan payment page including instructions for paying for the subscription plan selected by the user on the subscription plan page;

in response to the user paying for the subscription plan selected the by user on the subscription plan page, displaying to the user, via the first graphical user interface, a massage experience settings page including a plurality of selectable icons for customizing a desired massage experience program, wherein the massage experience settings page comprises a silhouette of a human body, wherein the silhouette is divided into three regions wherein the user may select the desired massage experience for each region via the plurality of selectable icons, wherein the user may select for each region a percentage of time to be massaged, an amount of pressure generated by the water jet system, a speed generated by the water jet system, and a number of waves generated by the water jet system;

in response to the user customizing the desired massage experience program, displaying to the user, via the first graphical user interface, the availability status information of each therapy room of the plurality of therapy rooms based on communication with the control system of each therapy room of the plurality of therapy rooms;

in response to at least one therapy room of the plurality of therapy rooms being available, display to the user, via the first graphical user interface, at least one selectable icon for selecting the at least one therapy room of the plurality of therapy rooms being available;

in response to the user selecting the at least one available therapy room, uploading the desired massage experience program, via the first graphical user interface, to the control system of said at least one available therapy room;

controlling water jets, via the control system, based on selections made by the user on the massage experience settings page to perform the desired massage experience program, providing a second graphical user interface in each therapy room of the plurality of therapy rooms such that the user can view and interact with the second graphical user interface while the desired massage experience program is in progress, wherein the second graphical user interface is configured to communicate with the control system, wherein the control system is configured to operate the water jet system based on inputs received at the second graphical user interface;

displaying to the user, via the second graphical user interface, a massage experience adjustment page for the user to modify the desired massage experience program while the desired massage experience program is in progress, the massage experience adjustment page comprising:

massage status information, wherein said massage status information includes time remaining for the desired massage experience program, and a plurality of selectable icons for modifying aspects of the desired massage experience program, wherein said modifying aspects include the region, the massage pressure generated by the water jet system, the massage speed generated by the water jet system, and a direction of the water expelled by the water jet system, and controlling the water jets, via the control system, based on selections made by the user on the massage experience adjustment page to modify the desired massage experience program while the desired massage experience is in progress.

9. The method of claim 8, wherein the massage experience settings page further comprises a drag icon configured to allow the user to select one region of focus for the entirety of the desired massage experience by dragging the drag icon to the one region of focus.

* * * * *